US012746344B2

(12) United States Patent
Plumptre et al.

(10) Patent No.: US 12,746,344 B2
(45) Date of Patent: Sep. 29, 2026

(54) CARTRIDGE ASSEMBLY FOR A DRUG DELIVERY DEVICE AND DRUG DELIVERY DEVICE

(71) Applicant: Sanofi, Paris (FR)

(72) Inventors: David Aubrey Plumptre, Warwick (GB); Robert Veasey, Warwick (GB); Paul Roger Griffin, Warwick (GB); Rory James Livingston Hawkins, Warwick (GB); Charles Henry Bertinat, Warwick (GB)

(73) Assignee: Sanofi, Paris (FR)

( * ) Notice: Subject to any disclaimer, the term of this patent is extended or adjusted under 35 U.S.C. 154(b) by 924 days.

(21) Appl. No.: 17/787,066

(22) PCT Filed: Dec. 16, 2020

(86) PCT No.: PCT/EP2020/086321

§ 371 (c)(1),
(2) Date: Jun. 17, 2022

(87) PCT Pub. No.: WO2021/122671

PCT Pub. Date: Jun. 24, 2021

(65) Prior Publication Data

US 2023/0036681 A1 Feb. 2, 2023

(30) Foreign Application Priority Data

Dec. 18, 2019 (EP) .................................... 19306673

(51) Int. Cl.
*A61M 5/34* (2006.01)
*A61M 5/24* (2006.01)

(52) U.S. Cl.
CPC ................ *A61M 5/34* (2013.01); *A61M 5/24* (2013.01); *A61M 2005/2437* (2013.01)

(58) Field of Classification Search
CPC .. A61M 5/34; A61M 5/24; A61M 2005/2437; A61M 2005/2433;
(Continued)

(56) References Cited

U.S. PATENT DOCUMENTS

| | | | |
|---|---|---|---|
| 5,000,744 | A | 3/1991 | Hoffman et al. |
| 2003/0004466 | A1 | 1/2003 | Bitdinger et al. |

(Continued)

FOREIGN PATENT DOCUMENTS

| | | | |
|---|---|---|---|
| CN | 103732278 A | 4/2014 | |
| EP | 3597237 | 1/2020 | |

(Continued)

OTHER PUBLICATIONS

International Preliminary Report on Patentability in International Appln. No. PCT/EP2020/086321, mailed on Jun. 30, 2022, 9 pages.

(Continued)

*Primary Examiner* — Lauren P Farrar
(74) *Attorney, Agent, or Firm* — Fish & Richardson P.C.

(57) ABSTRACT

The disclosure relates to a cartridge assembly for a drug delivery device, the cartridge assembly comprising a cartridge containing a drug; a cartridge holder, the cartridge holder defining an interior cartridge holding section, where the cartridge is arranged within the cartridge holding section, wherein the cartridge holder comprises a distal region with a needle connector arranged at a distal end of the distal region and a main body region; a fixing feature which is arranged at the distal region; and a region with reduced mechanical stiffness compared to the stiffness of the main body region, the region with reduced mechanical stiffness being integrated into the distal region and arranged between the needle connector and the fixing feature, such that when the cartridge is moved in a proximal direction, an emerging
(Continued)

load is transferred from the cartridge to the fixing feature and to the main body region in the proximal direction.

18 Claims, 15 Drawing Sheets

(58) Field of Classification Search
CPC .......... A61M 5/347; A61M 2005/2407; A61M 2005/2488
See application file for complete search history.

(56) References Cited

U.S. PATENT DOCUMENTS

| | | | | |
|---|---|---|---|---|
| 2013/0046245 | A1 | 2/2013 | Raab et al. | |
| 2013/0226082 | A1 * | 8/2013 | Klintenstedt | A61M 5/00 604/93.01 |
| 2014/0121606 | A1 | 5/2014 | Jugl et al. | |
| 2018/0169340 | A1 | 6/2018 | Aneas | |

FOREIGN PATENT DOCUMENTS

| | | | | |
|---|---|---|---|---|
| JP | 2002-509469 A | | 3/2002 | |
| JP | 2013-517870 A | | 5/2013 | |
| KR | 10-2015-0003199 A | | 1/2015 | |
| KR | 10-1772855 B | | 8/2017 | |
| RU | 2557896 C2 | | 7/2015 | |
| WO | WO 1999/016487 | | 4/1999 | |
| WO | WO 2011/092326 | | 8/2011 | |
| WO | WO-2011092326 A1 | * | 8/2011 | A61M 5/24 |
| WO | WO 2012/017035 A1 | | 2/2012 | |
| WO | WO 2013/153011 A1 | | 10/2013 | |
| WO | WO 2016/193313 | | 12/2016 | |

OTHER PUBLICATIONS

International Search Report and Written Opinion in International Appln. No. PCT/EP2020/086321, mailed on Feb. 19, 2021, 10 pages.
Gagnier et al., "Visual completion from 2D cross-sections: Implications for visual theory and STEM education and practice," Cognitive Research: Principles and Implications, Sep. 22, 2016, 1(1):9, 18 pages.

* cited by examiner

CARTRIDGE ASSEMBLY FOR A DRUG DELIVERY DEVICE AND DRUG DELIVERY DEVICE

CROSS REFERENCE TO RELATED APPLICATIONS

The present application is the national stage entry of International Patent Application No. PCT/EP2020/086321, filed on Dec. 16, 2020, and claims priority to Application No. EP 19306673.5, filed on Dec. 18, 2019, the disclosures of which are incorporated herein by reference.

TECHNICAL FIELD

The present disclosure relates to a cartridge assembly, particularly a cartridge assembly for a drug delivery device, preferably an injection device and/or a pen-type device, such as a pen-type injector. Furthermore, the present disclosure relates to a drug delivery device comprising the cartridge assembly.

BACKGROUND

In regular drug delivery devices, where a single drive mechanism which may be housed in a housing of the drug delivery device is used in conjunction with several cartridges or ampules to dispense drug contained in the cartridge or ampule from the device, usually a cartridge holder of the device is releasably connected to the housing and can be removed from the housing to replace a used cartridge. For doing so, the cartridge holder is disconnected from the housing, the used cartridge is removed from the holder and replaced with a new cartridge which is inserted into the cartridge holder, where the cartridge holder is again attached to the housing and the device is ready to be used again to dispense drug from the new cartridge.

Devices of this kind, however, do have several risks. For example, a cartridge containing a drug for which the mechanism of the drug delivery device is not specifically designed, i.e. a wrong drug, can be inserted into the cartridge holder and the user does not realize that he has put the wrong drug cartridge into the cartridge holder. This mistake may be lethal for the user and is also likely to occur as cartridges with different drugs usually look pretty much alike. Furthermore, the cartridge, if sold as a separate item, bears some risk to be damaged, in particular as the standard cartridges are usually glass cartridges.

SUMMARY

The present disclosure relates to the design of a cartridge fixing system which is used within a drug delivery device.

Certain aspects provide an improved cartridge assembly for a drug delivery device and/or further improvements or configurations associated with the cartridge assembly. One advantage for the techniques described in the present disclosure is that the described techniques can increase the stability of a cartridge being secured in the cartridge holder against attempts to remove the cartridge from the holder. As will become apparent from the following description, this may be achieved by increasing the amount of load that travels along one or more load paths, especially within the cartridge holder, and/or to reduce the amount of load that travels along load paths that tend to cause outwards radial deflection of the fixing feature, in particular when an attempt is made to remove the cartridge from the cartridge holder.

One aspect of the present disclosure relates to a cartridge assembly, in particular one for a drug delivery device, such as a pen-type device and/or an injection device. Another aspect relates to the drug delivery device. The drug delivery device expediently comprises the cartridge assembly as described herein above and below and a housing.

The cartridge assembly may be releasably secured to the housing. Within the housing, a drive mechanism, which is preferably designed to drive a dispensing action in order to dispense drug from the cartridge, may be retained or at least one or more elements thereof, such as a piston rod.

The cartridge assembly comprises a cartridge. The cartridge assembly comprises a cartridge holder. The cartridge holder may define an interior cartridge holding section. The cartridge holding section may be delimited by the cartridge holder, in particular by one or more parts thereof, circumferentially. The cartridge is expediently arranged within the cartridge holding section. The cartridge assembly further comprises a fixing feature. The fixing feature is expediently arranged to abut or abuts a cartridge surface of the cartridge, in particular a radially oriented surface. The fixing feature may be arranged to prevent removal of the cartridge from the cartridge holder. Thus, the cartridge may be permanently secured in the cartridge holder. The fixing feature may be arranged to prevent removal of the cartridge from the cartridge holder via an opening of the cartridge holder, preferably a proximal opening. This opening may be the one via which the cartridge is inserted into the cartridge holder, for example when assembling the cartridge assembly. The cartridge surface may be a proximal surface which faces away from the dispensing end of the cartridge.

The cartridge holder comprises at least two exterior regions. The exterior regions may comprise or may be a distal region and a main body region. The distal region may be arranged closer to the dispensing end of the cartridge than the main body region. The distal end wall of the cartridge holder may delimit the distal region distally. At the distal end of the distal region a needle connector is arranged. The main body region may retain the main body portion of the cartridge. The distal region may, within its interior, retain the head portion of the cartridge.

The fixing feature is arranged at the distal region. The cartridge holder comprises a region with reduced mechanical stiffness compared to the stiffness of the main body region. The region is integrated into the distal region and arranged between the needle connector and the fixing feature, such that when the cartridge is moved in the proximal direction an emerging load is transferred from the cartridge to the fixing feature and further to the main body region in the proximal direction. The region may be aligned at the circumference of the distal region, the main body region or a shoulder region which is aligned between the distal region and the main body region. In contrast to a known technical solution as shown in FIGS. 3A and 3B the region with reduced mechanical stiffness according to the disclosure may be positionally fixed. The region with reduced mechanical stiffness may be arranged at a position with respect to the shoulder region and/or the distal region. By positionally fixed it can be understood that the region with reduced mechanical stiffness remains in the position with respect to the shoulder region and/or the distal region where it has been arranged. In contrast the flexible arm shown in FIGS. 3A and 3B can flex out in radial direction.

Advantageously a transfer of the load to the distal region is kept as small as possible or avoided completely. Due to the integration of the region with reduced mechanical stiffness into the distal region a continuous mechanical connection of the fixing feature to the distal region of the cartridge holder in the circumferential direction may be achieved and access to the fixing feature, e.g. for tampering with the fixing feature, may be impeded.

During assembly, the fixing feature may more easily flex outwards due to the region with reduced stiffness and allows a cartridge septum retainer to move into the assembled position. The load path of the fixing feature is altered in the proximal direction for the situation if the cartridge is forced in the proximal direction relative to the cartridge holder, as may occur if the sub-assembly is dropped, or if a user attempts to remove the cartridge from the cartridge holder. The fixing feature is profiled such that the cartridge may be assembled easily and simply by the application of axial load to the cartridge.

The cartridge contains a drug or medicament. The cartridge comprises a dispensing end. Through the dispensing end, drug or medicament may be dispensed from the cartridge. The dispensing end of the cartridge may be designated as the distal end.

The altered load path increases the tendency of the fixing feature to flex inwards, and reduces the tendency of the feature to flex outwards in these scenarios. This increases the fixing strength provided by the fixing feature.

Further the disclosure allows a repeatable and reliable assembly of the cartridge into the cartridge holder by the insertion of the cartridge in the distal direction and application of force to the cartridge only in the distal direction, as provided by standard cartridge assembly equipment.

It robustly retains the cartridge within the cartridge holder against use and foreseeable misuse scenarios.

The region with reduced mechanical stiffness may comprise a groove or an aperture. Providing a groove has the advantage that the cartridge holder is closed towards the environment. The shape and the depth of the groove determines the stiffness of the material in this region. A larger and deeper groove provides a reduced stiffness compared to a smaller and less deep groove. An even further reduced stiffness may be achieved with an aperture which comprises a complete removal of material through its thickness which comprises an aperture. The groove or the aperture may comprise a rectangular or rounded rectangular shape. The groove or aperture may be aligned adjacent to the main body portion. The cartridge holder may comprise a shoulder region which is arranged between the distal region and the main body region. In this case the groove or aperture may be arranged adjacent to the shoulder region in the distal direction.

The fixing feature comprises a fixing surface, in particular a radially oriented surface. The fixing surface is expediently arranged to abut or abuts a cartridge surface of the cartridge, in particular a radially oriented surface. The fixing surface may be arranged to prevent removal of the cartridge from the cartridge holder. Thus, the cartridge may be permanently secured in the cartridge holder.

The fixing surface may be arranged to prevent removal of the cartridge from the cartridge holder via an opening of the cartridge holder, preferably a proximal opening. This opening may be the one via which the cartridge is inserted into the cartridge holder, for example when assembling the cartridge assembly. The cartridge surface may be a proximal surface which faces away from the dispensing end of the cartridge. The fixing surface may face the cartridge surface.

The fixing feature and, in particular, the fixing surface may abut, be arranged to abut or mechanically cooperate with the cartridge, particularly the cartridge surface, to secure the cartridge in the cartridge holder. The cartridge surface may be arranged between the dispensing end of the cartridge and the end opposite of the dispensing end. Particularly, the cartridge surface may be a surface which is different from an end surface of the cartridge, where two end surfaces, e.g. a distal end surface and a proximal end surface, delimit the cartridge in its main longitudinal direction of extent. The fixing feature may be integrated into the cartridge holder. The fixing feature may be a snap feature or a clip feature, for example.

In an embodiment, the fixing feature secures the cartridge axially within the cartridge holder. In particular, proximal movement of the cartridge relative to the cartridge holder may be prevented by the fixing feature. The fixing surface may abut the cartridge surface permanently. Particularly, the cartridge may be axially fixed in the cartridge holder on account of the fixing feature. Distal movement of the cartridge relative to the cartridge holder may be prevented by a proximal surface of the cartridge holder, e.g. an inner surface of the distal end wall. The proximal surface may be distally offset from the fixing surface. The proximal surface and the fixing surface may be adjusted such that a portion of the cartridge, such as the head portion, is, preferably tightly, received between the fixing surface and the proximal surface. In case the portion of the cartridge is tightly received between the surfaces, an additional elastic biasing member, such as a cartridge bias spring, which biases the cartridge distally relative to the cartridge holder in order to account for mechanical play between components can be avoided. Alternatively, the cartridge is axially moveable relative to the cartridge holder, e.g. on account of the proximal surface and the fixing surface being separated by a distance greater than the axial extension of the portion of the cartridge received between them. In this case, there may be provided a, preferably elastic, biasing member, e.g. in the drug delivery device, which biases the cartridge distally relative to the cartridge holder, i.e. it maintains a distal surface of the cartridge in abutment with the cartridge holder, e.g. the proximal surface of the cartridge holder. In this case, the cartridge surface may be arranged at a distance with respect to the fixing surface. The biasing member may be a spring washer or another elastically deformable member. The biasing member may abut the cartridge, i.e. there may be direct contact, or transfer the force to the cartridge indirectly, e.g. via a spacer. The biasing member may maintain a distance between the fixing surface and the cartridge surface.

The cartridge may be a glass cartridge.

In an embodiment, the fixing feature protrudes from an interior wall of the cartridge holder, particularly in the radial direction. In this way, a diameter of the interior of the cartridge holder may be reduced to a value below the exterior diameter of the cartridge and, particularly of the head portion of the cartridge. The fixing feature may be oriented in the radial direction or oblique with respect to the radial and the axial direction.

In an embodiment the fixing surface comprises an elevation which faces towards the cartridge surface. The elevation may be at the edge of the fixing feature or in the center. The cartridge surface may comprise a convex shape, preferably with its maximum in the center. The contact of the fixing surface to the cartridge surface is made at the center of the fixing surface.

In an embodiment the fixing surface may be sloped and/or oblique relative to the axial and radial direction. The fixing surface may be oriented relative to the cartridge surface, such that the surfaces are facing each other and are not parallel to each other. The fixing surface may contact the cartridge at the radially inboard edge of the fixing feature.

In an embodiment the fixing feature comprises a region with reduced thickness compared to the thickness of the main body region. This can be achieved by removing material from its radial outmost part. This leads to a reduced stiffness in this region and more flexibility of the fixing feature.

In an embodiment, the region with reduced mechanical stiffness overlaps angularly, axially and/or radially with the fixing feature.

In an embodiment, the region with reduced mechanical stiffness is restricted to the region distal from the fixing feature.

In an embodiment, a (sub-)section of the region with reduced mechanical stiffness or the entire region is radially outwardly offset from the fixing feature. The (sub-)section may be connected to another (sub-)section of the region of reduced mechanical stiffness, e.g. an opening, which is distally offset from the fixing feature.

In an embodiment, the cartridge holding section comprises at least three interior regions, i.e. a first region, a fixing feature region and a second region. The fixing feature, expediently, is arranged in the fixing feature region. The fixing feature region may be arranged between the first region and the second region, particularly as seen in the axial direction. An inner diameter, preferably the minimum inner diameter, or clear span of the cartridge holder in the fixing feature region is preferably less than the inner diameter, preferably the minimum inner diameter, or clear span in the first region and the inner diameter, preferably the minimum inner diameter, or clear span in the second region. The first region and the second region may have different and/or constant inner diameters or clear spans. Accordingly, the fixing feature may define a region of reduced inner diameter. As already explained above, this inner diameter is preferably less than the outer diameter of the head portion of the cartridge. The first region may be the region of the cartridge holder in which the head portion should be arranged and the second region may the region in which the main body portion of the cartridge should be arranged. The axial extension of the first and second regions may be different. The axial extension of the second region may be greater than the axial extension of the first region. The fixing surface may delimit the first region proximally. If the fixing feature is arranged in a region, where the inner diameter of the interior of the cartridge holder changes anyway, the fixing feature may be particularly easily implemented by injection molding. Core pins used during injection molding which define the respective interior region of the cartridge holder in a molding tool might need only a slight adjustment such that the fixing feature can be integrated into the cartridge holder in a region where the pins having different diameters meet. Injection molding is particularly suitable for high volumes.

In an embodiment, the cartridge holding section of the cartridge holder comprises a distal interior region. The distal interior region may be arranged distally relative to the fixing surface of the fixing feature. That is to say, the distal interior region may be that region of the interior of the cartridge holder, where the head portion of the cartridge is to be situated in the cartridge assembly when the cartridge has been guided into the cartridge holder. In the distal interior region, a cartridge guiding feature may be provided. The cartridge guiding feature may protrude in the radial direction from an inner wall of the cartridge holder, the inner wall being arranged in the distal interior region. The cartridge guiding feature may be provided to cooperate with the cartridge, e.g. with the septum retainer, in order to move the cartridge, in particular its head portion, radially relative to the fixing surface. The cartridge guiding feature may be angularly offset from the fixing feature and/or the fixing surface. The cartridge guiding feature may be provided opposite to the fixing feature. If a plurality of fixing features are provided, the number of cartridge guiding features may be less than or equal to the number of fixing features. One cartridge guiding feature may be sufficient, however, regardless of the number of fixing features. The cartridge guiding feature may be distally offset from the fixing feature. In other words, there may be an axial clearance between the cartridge guiding feature and the fixing surface. The distal interior region is expediently designed to receive the head portion of the cartridge. Thus, it may correspond to the first region of the cartridge holder discussed above. The distance by which the cartridge guiding feature is distally offset from the fixing surface and/or the fixing feature may be greater than or equal to the axial dimension or extension, e.g. the thickness, of the septum of the cartridge. Alternatively or additionally, the distance by which the cartridge guiding feature is distally offset from the fixing surface and/or the fixing feature may be less than the axial dimension or axial extension of the head portion of the cartridge. The head portion may include a head portion of a cartridge body, the septum and a septum retainer, such as a metal sleeve, by which the septum is permanently connected to the cartridge body. By providing the guiding feature at such a distal offset it can be achieved that the septum of the cartridge passes the fixing feature of the fixing surface before the cartridge co-operates with the guiding feature which is arranged to move the cartridge radially relative to the fixing surface such that the overlap between the fixing surface and the cartridge surface which is provided to interact with the fixing surface to retain the cartridge in the cartridge holder is increased.

The exterior distal region may correspond to the first interior region and the main body region may correspond to the second interior region with respect to the axial positions along the extension of the cartridge holder from the proximal opening to the distal end. An outer diameter of the cartridge holder may be less in the distal region than in the main body region. The fixing surface and/or the fixing feature may be arranged at an axial position, in particular as seen along the cartridge holder. The axial position may be situated in the distal region of the cartridge holder. Accordingly, the fixing surface may be arranged in the interior of the cartridge holder at a position which overlaps with the distal region, which may have a reduced outer diameter. Accordingly, the fixing feature region may overlap axially with the distal region at least partly.

In an embodiment one of the first region or the second region comprises a distal interior region which is arranged distally to the fixing feature, wherein the distal interior region comprises two regions with two different inner diameter, wherein the region with the smaller diameter of the two different diameter is arranged distally to the region with the larger inner diameter. The cartridge may be inserted into the cartridge holder along the distal direction through an opening at the proximal end of the cartridge. When moving in the distal direction the cartridge makes contact with the fixing feature. The fixing feature is arranged at the region of the cartridge holder with the larger inner diameter. When the cartridge is further moved in the distal direction it reaches the region with the smaller inner radius, such that the outer surface of the cartridge has a tighter contact with the inner wall of the cartridge holder compared to the region with a larger diameter.

The cartridge may have a main body portion and a head portion which are connected via a neck portion, which may have a reduced diameter as compared to the main body portion and/or the neck portion. The main body portion may be cylindrical. In the head portion, the dispensing end or opening of the cartridge may be arranged. The dispensing end or opening may be closed, e.g. by a, preferably pierce able and/or elastic, septum. The septum may be pierced by a needle to provide fluid communication between the interior of the cartridge and the exterior. The septum may be secured to a cartridge body of the cartridge, e.g. of glass. For example, the septum may be secured to the cartridge body by means of a septum retainer, e.g. a sleeve and/or of metal, such as a metal sleeve. The cartridge holder may have an opening which delimits the cartridge holder in the proximal direction. In the distal direction, the cartridge holder may be delimited by a distal end wall. A distal end face of the cartridge may be arranged to abut an interior proximal face of the cartridge holder. The proximal face may be in interior surface defined by the distal end wall. In other words, in the distal direction, the cartridge may not be moved relative to the cartridge holder. The cartridge may be secured permanently in the cartridge holder by the fixing feature. Preferably, without the fixing feature, the cartridge could be removed from the cartridge holder, e.g. via the proximal opening. The fixing surface may be a distal surface of the fixing feature, i.e. a surface facing in the distal direction, e.g. away from the proximal opening of the cartridge holder.

As the fixing feature is integrated into the cartridge holder, e.g. unitary with a cartridge holder body, forming the fixing feature, it can be integrated into the regular manufacturing process of the cartridge holder, e.g. by injection molding, without having to produce a separate fixing member and perform separate assembling steps to position a fixing member relative to the cartridge and the cartridge holder appropriately so as to secure the cartridge within the cartridge holder.

In an embodiment, an outer surface or outer wall of the cartridge holder, e.g. a sidewall of the cartridge holder, extends along and/or covers the entire fixing feature, e.g. axially and/or angularly or azimuthally. In other words, the cartridge holder may be closed in the radial direction, e.g. by a sidewall, along the, preferably entire, angular or azimuthal extension of the fixing feature and/or along the, preferably entire, axial extension of the fixing feature. As opposed to a fixing feature which angularly or axially overlaps with an opening in the cartridge holder, such a configuration is easier to manufacture, e.g. by injection molding. As the fixing feature may be provided in a region where the cartridge holder does not have a radially extending opening, the fixing feature is not easily accessible from the outside as it would be, if it were overlapping with such an opening or defined by such an opening. This assists in preventing manipulations on the cartridge assembly.

The cartridge holder comprises alternatively or cumulatively to the region of reduced stiffness a region with an increased mechanical stiffness which may arranged adjacent to the fixing surface in the proximal direction and which decreases the radial flexibility of the cartridge holder in that region such that a movement of the cartridge in the proximal direction is impeded. The region with increased mechanical stiffness may be arranged at the inner- or outer side wall of the cartridge holder.

In an embodiment, the cartridge holder is a unitary part. Particularly, the cartridge holder may be an injection molded part. The cartridge holder which comprises the distal region and the main body region may then be formed as a single piece. Although the cartridge holder is formed as a single piece, it may nevertheless have an integrated fixing feature which cooperates with a proximal surface of the cartridge.

In an embodiment, the fixing surface is a plane surface.

In an embodiment, the cartridge holder has a distal end wall or distal end face. The distal end wall may be arranged to abut a distal surface of the cartridge. In particular, a proximal surface of the distal end wall may be arranged to abut a distal surface of the cartridge. The distal end wall may extend in the angular direction, in particular around the main longitudinal axis. The end wall may have or define at least one opening, e.g. only one opening or more than one opening. The opening may be delimited by angular surfaces of the distal end wall which face one another. The opening may be arranged at a position which radially and angularly overlaps with the fixing surface or the fixing feature. Particularly, the fixing surface and the opening may be provided at corresponding radial and angular positions but at different axial positions in the cartridge holder. Expediently, the fixing surface is proximally offset from the opening, in particular by a distance which corresponds to or is defined by the axial extension of the head portion.

In an embodiment, the angular and/or radial dimension of the at least one opening may determine the angular and/or radial dimension of the fixing surface. Preferably, the angular and/or radial dimension of the opening is greater than or equal to the angular and/or radial dimension of the fixing surface. In this way, the fixing feature may be defined by a molding tool which is guided through the region of the mold which is designed to define the distal end of the cartridge holder until the position is reached where the fixing feature should be arranged.

An advantage of the opening in the distal end wall of the cartridge holder is that in the region of the opening and the region axially extending therefrom towards and or up to the fixing feature, the radial flexibility of the cartridge holder may be increased. This facilitates that the cartridge holder is widened radially while the cartridge co-operates with the rigid fixing feature when the cartridge is inserted into the cartridge holder. When the head portion of the cartridge, for example, has passed the fixing feature the cartridge holder, on account of its own intrinsic elasticity, can resume its original non-deformed shape and the fixing surface can be arranged to abut the cartridge surface to secure the cartridge within the cartridge retaining section.

In an embodiment, the fixing feature is formed unitarily with a section or region of the cartridge holder. The section or region may define or form at least a section of the exterior surface or the outer contour of the cartridge holder. Thus, the fixing feature may be integrated into a region or section of the cartridge holder which defines the outer appearance of the cartridge holder.

As the cartridge is expediently permanently secured in the cartridge holder, the cartridge assembly may form one unit or a single unit of consumable material. That is to say, the cartridge assembly in its entirety may be a disposable item, which is disposed of after the drug or medicament in the cartridge has been dispensed, and substituted by a new cartridge assembly.

If the cartridge is permanently secured in the cartridge holder by the fixing feature several advantages are attained. For example, the cartridge is always protected by the cartridge holder when the user handles the cartridge assembly. The risk of a cartridge breaking is then considerably reduced as opposed to systems where the cartridge in the holder needs to be replaced by the user. Rather, in the proposed system, the entire cartridge assembly is replaced with a new one.

Moreover, as the cartridge assembly comprises not only the cartridge but also other elements like the cartridge holder, it is easier to dedicate or code the cartridge to a particular drive mechanism or housing for a drug delivery device, in particular without having to change the design of the cartridge.

The dedication or coding can be achieved via features provided on the exterior of the cartridge holder which may cooperate with features provided in the housing to either permit that the cartridge assembly is connected to the housing, if the drive mechanism housed in the housing matches the cartridge assembly or the drug or medicament contained therein or not if the wrong cartridge assembly is used. Alternatively or additionally, on the cartridge holder, additional information about the content of the cartridge can be presented such as the name of the active pharmaceutical ingredient, the brand name etc.

As the cartridge surface is provided between the two opposite ends of the cartridge, the disclosed concept can be used for cartridges of different lengths easily. Accordingly, a set of cartridge assemblies having at least two cartridge assemblies may have two different cartridges of different lengths in the assemblies.

In an embodiment, the cartridge surface is arranged closer to the dispensing end than to an end opposite of the dispensing end, i.e. the proximal end. This facilitates securing cartridges of different lengths in the cartridge holder and/or provides the fixing feature in a region which is not easily accessible from the outside, i.e. a region which is further away from the proximal opening or end of the cartridge holder than from the distal end of the cartridge holder. The cartridge surface may be arranged further away from the proximal end than 2/3*L, 3/4*L, 4/5*L, where L is the total length of the cartridge. The length of the cartridge may be defined or determined by the distance between the proximal end of the cartridge and the distal end or dispensing end.

In an embodiment, the cartridge surface is a surface which delimits the head portion axially, in particular in the proximal direction. The cartridge surface may extend circumferentially, e.g. flange-like along the entire circumference of the cartridge.

In an embodiment, the end of the cartridge opposite of the dispensing end is closed via a movable bung or stopper. If the bung or stopper is displaced within the cartridge towards the dispensing end, drug or medicament may be dispensed from the cartridge, provided fluid communication is established between the interior of the cartridge and the outside, e.g. by a needle piercing through the septum. The bung or stopper may be retained within the main body portion of the cartridge. Accordingly, as the cartridge surface with which the fixing feature should interact may be located at the head portion, the main body portion of the cartridge can be freely designed, such as with respect to length and/or diameter. This facilitates fixing or securing cartridges of different volumes in the cartridge holder. The bung or stopper expediently sealingly closes the cartridge proximally. The bung may be restricted to travel within the main body portion. That is to say, it may not enter the neck portion and/or the head portion.

In an embodiment, the fixing feature protrudes from an interior wall of the cartridge holder, particularly in the radial direction. In this way, a diameter of the interior of the cartridge holder may be reduced to a value below the exterior diameter of the cartridge and, particularly of the head portion of the cartridge. The fixing feature may be oriented in the radial direction or oblique with respect to the radial and the axial direction.

In an embodiment, the cartridge holder is configured such that the fixing feature can be, preferably resiliently, displaced in the radial direction, e.g. relative to the remainder of the cartridge holder. In this way, it is guaranteed that a section of the cartridge, in particular the head portion, can be guided past the fixing feature, thereby radially deflecting or displacing the fixing feature, e.g. outwardly. Once the head portion has passed the fixing surface, the fixing feature may be displaced back to its original non-displaced position, expediently on account of its resiliency and/or inwardly, and, thereafter, secure or lock the cartridge within the cartridge holder.

In an embodiment, the cartridge holder comprises a plurality of fixing features with associated fixing surfaces which are arranged to abut a, preferably a common, cartridge surface of the cartridge. The fixing features may be distributed circumferentially, preferably uniformly.

In an embodiment, the fixing feature has a proximal surface. The proximal surface may face away from the fixing surface. The proximal surface may be sloped and/or oblique relative to the axial and radial direction. The fixing surface may be oriented in the radial direction. A sloped proximal surface of the fixing feature facilitates guiding of the cartridge along the fixing feature and displacing the fixing feature when the cartridge travels along the fixing feature. The fixing surface is preferably more inclined relative to the main axis of the cartridge holder than the proximal surface and may extend perpendicular with respect to the axis.

In an embodiment, the fixing feature is arranged in a region of the cartridge holder, where the cartridge holder does not have an opening.

In an embodiment, in the region with the fixing feature, the cartridge holder is closed laterally, circumferentially and/or radially. Preferably, the cartridge holder is closed laterally and/or radially in the circumferential direction in the region of the fixing feature such as along its entire circumference.

In an embodiment, preferably in the distal region, the cartridge holder comprises a needle connector, where the needle connector comprises a connection feature, e.g. a thread or other connection means, the connection feature being suitable to or configured to connect a needle unit to the cartridge holder. The needle unit may comprise a needle hub and a needle carried by the needle hub. The needle may be secured to the needle hub and protrude distally from the hub. A proximal end of the needle may be designed to penetrate the septum of the cartridge. The needle may be of metal or steel and the needle hub may be of plastic. When the needle unit is connected to the needle connector, the needle may extend though a distal opening of the cartridge holder towards the septum of the cartridge and penetrate the septum to establish fluid communication with the interior of the cartridge. Then a dose of drug or medicament can be dispensed from the interior of the cartridge through the needle.

In an embodiment, the distal end wall defines a central or needle opening. The distal end wall may extend circumferentially or angularly around this opening. The needle opening may be connected with the opening of or in the distal end wall. Accordingly, manufacturing the cartridge holder via injection molding is facilitated as one continuous feature can be used which defines both openings, i.e. the needle opening and the opening of the distal end wall which corresponds to the position of the fixing surface.

In an embodiment, the cartridge holder is an injection molded piece and an injection gate is positioned on the distal end of the cartridge holder, in particular on the distal surface of the distal end wall.

The septum is usually deformable, e.g. elastically. Accordingly, if radial forces are transferred to the cartridge while the septum axially overlaps with the fixing feature, these forces could deform the septum and/or the septum retainer, which may be arranged between the septum and the fixing feature. Such forces may occur, when the cartridge is guided past the fixing feature and displaces the fixing feature radially. Thus, there is a risk that, if these forces would act on the septum, the cartridge could be damaged, e.g. by deforming the septum retainer or removing the septum from the cartridge body. This is undesirable, of course, as the cartridge could be damaged severely, if the forces act on the septum or the septum retainer. Accordingly, the cartridge and the cartridge holder are configured and adjusted to each other such that the fixing feature is displaced only by a radial force exerted by means of the cartridge, if it is arranged at a position relative to the cartridge which is proximally offset from the septum, i.e. when it overlaps with a section of the cartridge body. As the cartridge body is more rigid than the septum, the entire cartridge is more rigid in that region and the risk of damaging the cartridge is considerably reduced.

In an embodiment, the cartridge holder comprises just one fixing feature or a plurality of fixing features. If there are a plurality of fixing features, they are expediently uniformly distributed in the angular direction and/or axially aligned. Each of the fixing features expediently has one associated fixing surface which can abut the cartridge surface. The angular extension of the respective fixing feature or the associated fixing surface may be less than or equal to one of the following values: 20°, 15°, 10°.

In an embodiment, in the cartridge assembly, a distance between the cartridge surface and the fixing surface may be zero, i.e. the surfaces may be in abutment, or greater than zero, e.g. less than or equal to one of the following values: 2 mm, 1 mm, 0.9 mm, 0.8 mm, 0.7 mm, 0.6 mm, 0.5 mm, 0.4 mm, 0.3 mm. The distance may determine the amount of axial movement which is possible in the cartridge assembly. In case of a non-zero distance, this distance may be maintained by the biasing member when the assembly is used in a drug delivery device.

In an embodiment, the cartridge assembly comprises at least one connection feature, which is configured to be connected to a housing which may retain a drive mechanism, e.g. a feature for a threaded connection or a bayonet connection.

In an embodiment, the cartridge assembly comprises at least one interface or coding feature which is configured to be cooperate with a corresponding interface or coding feature on the housing. The connection feature and the interface or coding feature may be formed by the same feature or by different features. By means of the interface or coding features, a coding can be achieved such that the cartridge assembly can only be assembled to a housing with a matching coding feature. This increases the safety for the user and it ensures that the drive mechanism which is designed to dispense a specific drug or medicament or specific amounts of drug or medicament and the content of the cartridge in the cartridge assembly match. If the cartridge assembly and the drive mechanism do not match the interface or coding features on the housing and the cartridge assembly are incompatible and the cartridge assembly cannot be connected to the housing to form a drug delivery device.

The terms "distal" and "proximal" as used herein may refer to opposite axial directions or ends. "Distal" may refer to a direction towards the dispensing end or an end of a component of a drug delivery device which is or is to be arranged closest to the dispensing end of the cartridge, the cartridge assembly or the drug delivery device. "Proximal" may refer to a direction away from the dispensing end or an end which is or is to be arranged further away from the dispensing end of the cartridge, the cartridge assembly or the drug delivery device.

The terms "axial", "radial", "angular", or "azimuthal" as used herein may be used with respect to a main longitudinal axis of the device, cartridge, or cartridge assembly, e.g. the axis which extends through the proximal and distal ends of the cartridge assembly, the cartridge or the drug delivery device.

Features disclosed above in conjunction with the cartridge assembly or the drug delivery device should not be regarded as referring to only the recited aspect or embodiment. Rather, the features also apply for other embodiments or aspects. Features disclosed in conjunction with the assembly do also apply for the device and vice versa. Of course, features disclosed in specific embodiments, be it above or further below, can also be applied in combination with one another and/or with other features of other embodiments.

Further features, advantages and advantageous embodiments of the present disclosure will become apparent from the following description of the exemplary embodiments in conjunction with the drawings.

BRIEF DESCRIPTION OF THE FIGURES

Identical elements, elements of the same kind and identically acting elements may be provided with the same reference numerals throughout the figures.

DETAILED DESCRIPTION

Figure 1B:
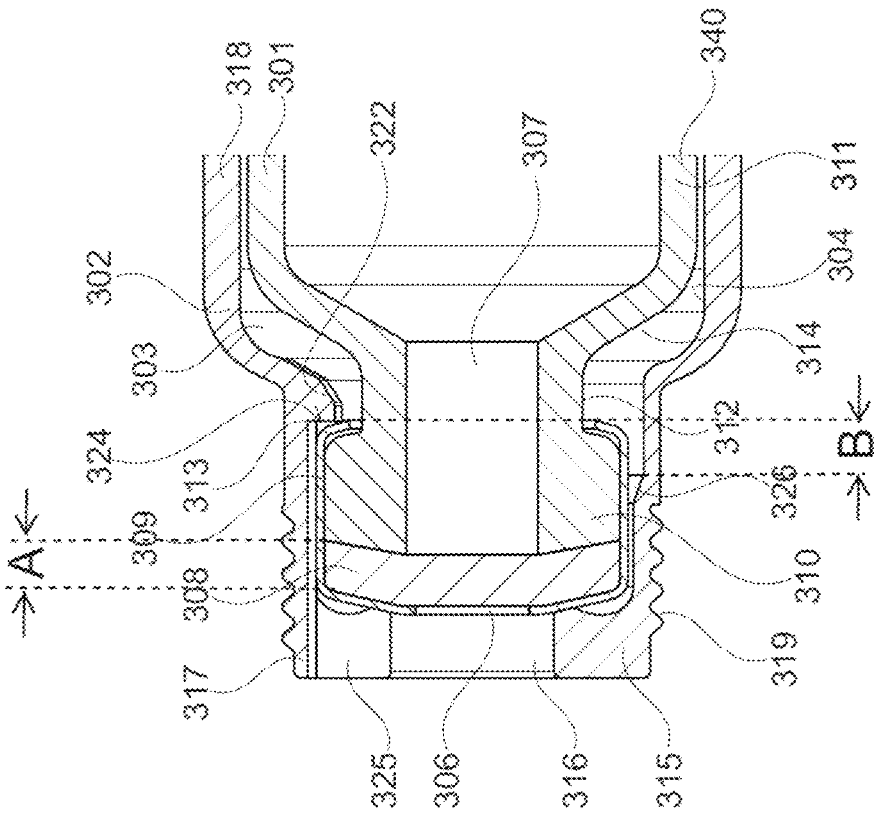
FIGS. 1A through 1F illustrate an embodiment of a cartridge assembly on the basis of a schematic perspective view in FIG. 1A and a schematic sectional view of the assembly in FIG. 1B, and different views of the cartridge holder without the cartridge being arranged therein in FIGS. 1C through 1F. The FIGS. 1A through 1F and their descriptions are disclosed in the European application 18305975.7.
Figure 1A:
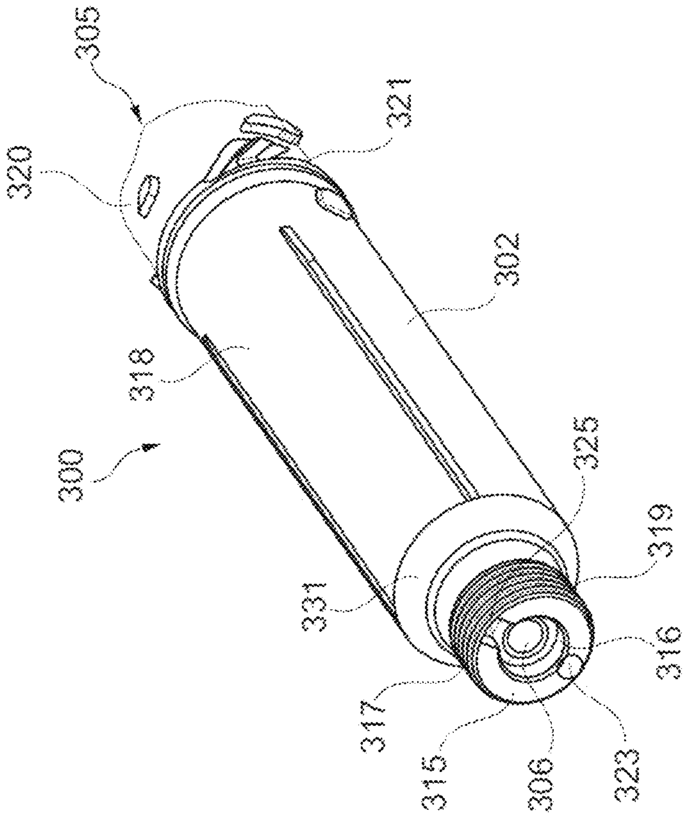

In the following, in conjunction with the drawings, several embodiments of cartridge assemblies with fixing features which are integrated into the cartridge holder of the assembly are disclosed. Before the specifics of the respective embodiments are disclosed, features which apply to all embodiments are discussed. FIGS. 1A through 1F each illustrate one embodiment of a cartridge assembly 300.

The cartridge assembly 300 comprises a cartridge 301 and a cartridge holder 302. The cartridge 301 is arranged within a cartridge holding or retaining section 303 of the cartridge holder. The cartridge retaining section is expediently delimited by an inner wall 304 of the cartridge holder 302, preferably circumferentially. The cartridge holder 302 has an opening 305. The opening 305 is expediently a proximal opening. The proximal opening may provide access to the interior of the cartridge holder from the proximal end of the holder. Via the opening 305, the cartridge 301 can be inserted into the cartridge holder. A dispensing end 306 of the cartridge may be inserted or introduced into the cartridge holder through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305. The axial extension of the cartridge holder is expediently chosen so as to cover at least 50%, preferably more than 60% or more than 70% such as more than 80% or more than 90% of the total length of the cartridge. The entire cartridge may be covered by the cartridge holder 302 as depicted in the embodiments.

The end of the cartridge opposite to the dispensing end 306, i.e. the proximal end, is not illustrated explicitly in the figures. This end may be closed by a movable bung or stopper, which is likewise not explicitly illustrated. The bung or stopper may sealingly close a proximal opening of the cartridge. A drug 307 or medicament is contained in that region of the cartridge which is arranged between the dispensing end and the bung. Drug may be dispensed through the dispensing end 306 from the cartridge, if fluid communication between the interior of the cartridge and the exterior is provided and the bung is moved towards the dispensing end. The amount of drug 307 in the cartridge is preferably sufficient for a plurality of doses, where the size of the dose may be set by the user or may be fixed, e.g. by the design of the drive mechanism used to deliver the drug from the drug delivery device which comprises the cartridge.

On the side of the dispensing end 306, the interior of the cartridge which holds the drug or medicament 307 is sealingly closed by a septum 308. The septum 308 may be retained at or fixed relative to a cartridge body 340 of the cartridge by means of a septum retainer 309. The septum 308 is expediently pierceable, e.g. via a needle, which may provide fluid communication between the interior of the cartridge and the exterior. The septum retainer 309 may be formed by a cap, e.g. a metal cap, such as an aluminum cap. The metal cap may be connected via clamping or crimping to the cartridge body 340. The body of the cartridge may be formed of glass. The body 340 may define the outer contour of the cartridge. In the region of the dispensing end 306, where the needle should penetrate the septum, an opening is provided in the septum retainer 309 to allow the needle to pass through the region of the septum retainer. The cartridge 301 comprises a head portion 310 and a main body portion 311. The head portion 310 is arranged on the side of the dispensing end 306. The main body portion 311 may be arranged closer to the proximal end of the cartridge than the head portion 310. Between the head portion 310 and the main body portion 311 a neck portion 312 may be arranged. The main body portion 311 may be that region, where the bung or stopper may travel. The main body portion has a tubular configuration. The neck portion 312 may have a reduced diameter, outer and/or inner diameter, as compared to the main body portion 311. The head portion 310 has a reduced diameter, outer and/or inner diameter, as compared to the main body portion 311. The neck portion 312 has a reduced diameter as compared to the main body portion and also with respect to the head portion 310. The diameter may be the extension of the cartridge 301 in a direction perpendicular to the main longitudinal axis of the cartridge or the cartridge assembly which extends between the proximal end and the distal end. The neck portion may extend circumferentially. The entire cartridge 301 may be rotationally symmetric relative to the main longitudinal axis. The transition between the head portion 310 and the neck portion 312 may be formed via a comparatively steep surface, which is preferably less inclined relative to the radial direction than the surface which is provided between the neck portion 312 and the main body portion 311. Accordingly, the transition between the neck portion 312 and the main body portion 311 may be less steep than the one between the head portion 310 and the neck portion 312.

Specifically, a cartridge surface 313, which may delimit the head portion 310 proximally, may have an inclination relative to the radial direction which is less than the inclination of a shoulder surface 314 which delimits the main body portion distally. The cartridge surface may be formed by the septum retainer 309 or, alternatively by the cartridge body 340. The septum retainer 309 may clamp the septum to the cartridge body. Thus, the septum retainer may extend from the distal end along the cartridge to a surface of the neck portion of the cartridge body facing away from the distal end of the cartridge and extending in the radial direction to clamp the septum 308 to the cartridge body. The cartridge may comprise or consist of the cartridge body 340, the septum 308, the septum retainer 309, the drug or medicament 307, and/or the bung (not explicitly illustrated).

The cartridge holder 302 comprises on that end opposite of the opening 305 and/or closest to the dispensing end 306 of the cartridge, i.e. its distal end, a distal end wall 315. The distal end wall may extend circumferentially in a ring-like fashion. A proximal surface of the distal end wall 315 is arranged to abut the distal end face of the cartridge 301. In this way, the cartridge 301 can be retained in the cartridge holder without moving distally relative to the cartridge holder 302. The distal end wall 315 may define an opening 316 in the cartridge holder. The end wall may extend around the opening such that the opening is a central opening in the end wall. The opening may extend axially through the distal end wall 315. The opening 316 may be provided such that a needle can be guided through the opening towards the cartridge, in particular towards the septum 308.

The cartridge holder 302 may comprise a distal region 317 and a main body region 318. The distal region 317 is arranged closest to the dispensing end of the cartridge and/or to the distal end wall 315 of the cartridge holder. The main body region 318 is arranged further away from the distal end or the distal end wall 315 and/or closer to the opening 305 than the distal region. As compared to the main body region the distal region may have a reduced outer diameter. The reduction may be determined by the reduced diameter of the head portion as compared to the diameter of the main body portion of the cartridge. The main body region 318 and the distal region may be connected by an inwardly directed shoulder region 331. In the distal region a needle connector 319, for example a thread may be arranged. Via the needle connector, a needle unit, for example a hub of a needle unit may be secured to the cartridge holder 302. A needle retained in the needle hub may be guided through the opening 316, pierce the septum 308 and provide fluid communication to the interior of the cartridge to dispense drug 307 or medicament from the cartridge 301. The distal region 317 may be designed to receive the head portion 310 of the cartridge 301 in its interior. The main body region 318 may be designed to receive the main body portion 311 of the cartridge. On the side of the proximal end the cartridge holder may have a connection or interface region 320. In that region, connection or interface features may be provided, which are configured to cooperate with corresponding features on a housing 10 to connect the cartridge assembly 300 to the housing to form a drug delivery device 1 (see FIGS. 12 and 13). The connection features may be designed for a threaded or bayonet connection between cartridge holder and housing. Preferably, the connection or interface features are coded to a housing which houses a drive mechanism designed for the drug or medicament contained in the cartridge of the cartridge assembly. The coding ensures that only a correct cartridge assembly can be assembled to the housing to form a drug delivery device. In this way, it can be guaranteed that the drug in the cartridge assembly is dispensed using a drive mechanism which is specifically designed to dispense the content of the cartridge. The drive mechanism may comprise a piston rod, which is arranged to drive the bung or stopper distally relative to the cartridge, causing drug or medicament to be dispensed from the cartridge.

Between the proximal end and the distal end of the cartridge holder 302, preferably closer to the proximal end than to the distal end, a radially outwardly protruding step 321 or flange, may be provided. The step or flange 321 may extend over the entire circumference of the cartridge holder 302. A proximal surface of the step 321 may be arranged to contact a distal surface of the housing when the cartridge assembly is connected to the housing. The connection region 320 may be covered by the housing, when the assembly has been connected to the housing. The main body region 318 and the distal region 317 may, however, protrude from the housing.

Furthermore, the cartridge holder 302 comprises at least one fixing feature 322. As seen along the axial direction, the fixing feature 322 is provided between two interior regions of the cartridge holder, where one is adapted to receive and retain the head portion 310 and another one is adapted to receive and retain the main body portion 311 of the cartridge. The fixing feature 322 may extend in the region of the neck portion of the cartridge 301. The fixing feature 322 protrudes radially from an inner wall of the cartridge holder 302. Preferably, the fixing feature 322 reduces the inner diameter of the cartridge holder such that in that region, the inner diameter is less than the outer diameter of the head portion of the cartridge.

Therefore, if the head portion of the cartridge should be guided axially past the fixing feature from the proximal opening, the fixing feature has to be deflected radially outwardly, e.g. displaced only radially. If the fixing feature is deflected, the head portion can pass the fixing feature. Preferably, the fixing feature is deflected by means of the head portion cooperating with a proximal surface of the fixing feature which may be oblique, i.e. neither perpendicular nor parallel, with respect to the main axis of the cartridge holder. After the head portion has passed the fixing feature, the fixing feature may move radially inward again, e.g. resiliently. The interior region of the cartridge holder which is designed to receive the head portion 310 may have a reduced diameter as compared to that region which receives the main body portion 311.

The fixing feature 322 is formed integrally, e.g. by injection molding, with a section of the cartridge holder which defines an exterior surface or at least the outer contour of the cartridge holder. That is to say, if applicable the cartridge holder may be provided with a coating on the exterior surface whereas the outer contour may still be defined by the section of the cartridge holder the fixing feature is integrated into. In FIGS. 1A through 4A, an injection gate 323 is shown, which indicates the position where the fluid plastic compound is injected into a mold cavity which defines the shape of the cartridge holder. The injection gate 323 may be positioned in the region of the distal end wall 315 of the cartridge holder, particularly on a distal face of the distal end wall.

The fixing feature 322 comprises a fixing surface 324. The fixing surface 324 may be a distal surface of the fixing feature. Preferably, the fixing surface is radially oriented, i.e. it extends in the radial direction, and/or plane. The fixing surface 324 is arranged to abut or abuts a proximally facing surface of the cartridge, such as the cartridge surface 313. Thus, the cartridge surface 313 and the fixing surface 324 are arranged to prevent that the cartridge is removed proximally from the cartridge holder through the opening 305 by mechanical cooperation with one another. Accordingly, removal of the cartridge from the holder through the opening 305 is prevented by means of the fixing feature 322. The fixing feature 322 may be formed as a snap and/or clip feature. The angular extension of the fixing feature or the fixing surface may be less than or equal to one of the following values: 20°, 15°, 10°, in alternative embodiments equal or greater than 20°, for example 30°, 35°, 40°, 45°, 50°, 55° or 60°. For example the angular extension may be between 10° and 60°.

Furthermore, an outer wall of the cartridge holder is provided at the axial position of the fixing feature. Thus, the cartridge holder is closed at least in the region of the fixing feature. Accordingly, the fixing surface and/or the fixing feature cannot be accessed from the outside. This reduces the chances that the cartridge assembly can be tampered with.

In the following, an embodiment of a cartridge holder with a fixing feature integrated into the cartridge holder is discussed in more detail. The embodiment depicted in FIGS. 1A and 1B, has one fixing feature 322, in particular just one. Of course, a plurality of fixing features could be provided as well.

The fixing feature 322 protrudes radially from the inner wall 304 of the cartridge holder 302. The fixing feature 322 is arranged in the interior of the distal region 317 of the cartridge holder 302 and, particularly, in the interior region of the cartridge holder where the needle connector 319 is provided on the exterior. As is apparent from FIG. 1A and also from FIG. 1B, the distal end wall 315 which has a generally ring-like configuration, has an opening 325. The opening 325 is radially oriented and interrupts the ring defined by the distal end wall 315. The opening 325 extends radially outwardly from the opening 316. The angular and radial position of the opening 325 may correspond to the fixing feature 322 or the fixing surface 324, where the opening is axially offset from the fixing feature, e.g. in the distal direction. Particularly, as seen from the distal end along the axis, the fixing surface may be visible from the distal end. The fixing surface may be framed radially and angularly by sidewalls which delimit the opening 325. In the figures, the head portion 310 of the cartridge 301 is arranged between the opening 325 and the fixing surface 324. The angular dimension and/or the radial dimension of the opening 325 may define, may correspond to or may be greater than the angular dimension and/or the radial dimension of the fixing surface and/or the fixing feature. Providing an opening in the region of the distal end facilitates molding of the cartridge holder with the integrated fixing feature with only minor modifications to the mold or molding tool as compared to a cartridge holder without fixing features. In a cartridge holder without a fixing feature, two core pins of different diameters may be used for producing the cartridge holder by injection molding, where one core pin defines the interior of the distal region and one core pin defines the interior of the main body region 318 of the cartridge holder. A short core pin may define the interior in the distal region and a long core pin may define the region of the interior in the main body region. The fixing feature 322 may be integrated right at the intersection or the boundary of the two different core pins of the injection molding tool. The opening 325 may be formed during the molding process and facilitates the molding of a cartridge holder with the fixing features 322 integrated into it. The opening 325 may be defined by a protrusion, e.g. of metal, on the short core pin.

In the region where the fixing feature 322 is provided, e.g. the distal region 317, the cartridge holder 302 may be radially deformable. Thus, the inner diameter may be increased when the cartridge holder 302 is exposed to an axially or radially outwardly directed force. The capability of the cartridge holder 302 to be radially deformed when exposed to a radially directed force may be increased in that angular section of the distal region 317 which overlaps angularly with the opening 325. The fixing feature 322 is arranged in this region as it overlaps angularly with the opening. The fixing feature is expediently non-flexible and/or rigid, e.g. more rigid than the distal region 317 or the inner wall of the first region where the head portion of the cartridge is to be arranged. Thus, when an axial and/or radial force acts on the fixing feature 322, e.g. while the head portion is guided along and in contact with the fixing feature 322, the cartridge holder 302 is widened on account of the rigidity of the fixing feature 322. The fixing feature 322 itself is not deformed or flexed or at least not significantly deformed as compared to that portion of the cartridge holder which is deformed, e.g. the distal region 317 or the shoulder region 331. As the cartridge holder 302 is expediently of plastic, deformation of the fixing feature itself to a very limited degree cannot be avoided. However, in the proposed concept, it is the widening of the cartridge holder in a circumferentially closed region of the cartridge holder 302 which facilitates insertion of the cartridge into the cartridge holder. The cartridge holder is deformed when the cartridge is introduced into the cartridge holder. The region which is deformed expediently is a region which does not have flexible arms, tongues, or tab-like features. The fixing feature 322 is used to transfer the insertion force of the cartridge to the cartridge holder in order to widen the cartridge holder laterally. The interior of the cartridge holder is widened in the region of mechanical contact between the cartridge and the cartridge holder, i.e. in the region in which the fixing feature is disposed, and preferably in axially and/or circumferentially adjacent regions. As opposed to deflecting distinct flexible arms, tongues, or tab-like features, widening the interior of the cartridge holder may provide a more stable fixation of the cartridge in the cartridge holder once the cartridge has been introduced into the cartridge holder. After the head portion 310 has passed the fixing feature 322, the fixing feature is displaced inwardly again, e.g. on account of the deformation being an elastic deformation, and the cartridge surface 313 and the fixing surface 324 are arranged as depicted in FIG. 1B. The fixing feature is preferably not or at least not significantly deformed during this process and, in particular, not axially deflected or pivoted.

As shown in FIG. 1B, distally offset from the fixing surface 324, a sloped surface 326 which rises radially along its extension in the distal direction, is arranged. By means of this surface, which is preferably arranged at the opposite side of the fixing surface or at least angularly offset from the fixing surface, a radial movement of the head portion 310 of the cartridge 301 may be achieved to a region overlapping radially with the fixing surface 324. Thus, the sloped surface acts as a cartridge guiding feature during the assembling process of the cartridge assembly 300. References to the sloped surface 326 may therefore be regarded as references to the cartridge guiding feature and vice versa. The radial overlap of the fixing surface 324 and the surface 313 of the cartridge 301 when the cartridge has reached its final position may be increased in this way. The sloped surface 326 may strengthen the stability of the securing of the cartridge in the cartridge holder, e.g. in case only one fixing feature is provided.

The distal offset (highlighted with "B" in FIG. 1B) of the cartridge guiding feature 326 from the fixing feature, from the fixing surface 324 and/or from a radial free end of the fixing feature 322 may be greater than the thickness (highlighted with "A" in FIG. 1B) of the septum 308 of the cartridge. This ensures that the septum retainer 309 is backed by the more rigid cartridge body 340 and preferably not by the septum, when the cartridge interacts with the fixing feature 322 to radially displace the feature outwardly in order to temporarily widen the interior of the cartridge holder. Thus, the force required to displace the fixing feature 322 is not transferred to the septum. If the force were transferred to the septum, the risk that the septum retainer 309, which may be a thin metal component, is deformed or the septum is damaged is considerably increased. This can be avoided by the distal offset between cartridge guiding feature 326 and the fixing surface 324 by more than the thickness of the septum 308. The distal offset B is expediently less than the axial extension of the head portion 310 of the cartridge. In this way, the cartridge guiding feature may property guide the cartridge 301 radially inwardly by cooperating with the head portion 310.

In the region of the interior of the cartridge holder 302 between the cartridge guiding feature 326 and the fixing surface 324, the inner diameter of the interior of the cartridge holder may be greater than in the region of the cartridge guiding feature and/or in a region distally offset from the cartridge guiding feature, if such a region is present which it may be or may not be. In the region of the interior of the cartridge holder between the cartridge guiding feature and the fixing surface the inner diameter may be greater than the inner diameter in the fixing feature region. In the region of the cartridge guiding feature 326 and/or distally with respect to the cartridge guiding feature, the inner diameter of the cartridge holder may be greater than the inner diameter in the fixing feature region, e.g. greater than or equal to the outer diameter of the head portion 310.

In other words, the septum retainer or metal sleeve 309 has a distal section which surrounds the soft septum 308, and a proximal section that surrounds the neck of the cartridge body or glass ampoule 340. It is advantageous if the distal section of the septum retainer has moved past the fixing surface 324 before the distal section makes contact with the cartridge guiding feature or sloped surface 326. In this way the radial overlapping of the metal sleeve 309 and the fixing surface is minimal during the period of assembly where the fixing surface could damage the metal sleeve 309, and this overlapping is only increased when the fixing surface has moved past the distal section of the metal sleeve 309 and is applying radial pressure to the proximal section. As the proximal section is supported by a harder, e.g. glass like, material than the distal section it will not be damaged or indented. The final overlapping between the fixing surface and the cartridge surface at the end of assembling process is still high. The final overlap may be defined by the smaller inner diameter of the cartridge holder in the region of the sloped surface which marks the end of the sloped surface 326.

When a cartridge holder 302 with an integrated fixing feature 322 was tested, it has been discovered, that the distal section of the septum retainer 309 dents badly unless the diameter prior to sloped surface 326 is sufficiently larger than the diameter after sloped surface 326 so that the cartridge 301 can move away from the fixing feature with minimal, if any, interference in the distal section of the septum retainer and that this interference only increases after the fixing feature is pressing in the region of the septum retainer 309 where the head portion of the cartridge body, e.g. of glass, backs up/supports the septum retainer, which may be a thin and easily deformable metal component.

When the cartridge 301 has been assembled into the cartridge holder 302, the fixing feature 322 may block proximal movement of the cartridge 301 relative to the cartridge holder 302. The fixing feature, however, expediently does not exert a securing force, e.g. a distally or radially directed force, onto the cartridge regularly but only prevents removal of the cartridge from the cartridge holder. In this way, the force load onto the cartridge may be advantageously low.

Figure 1C:
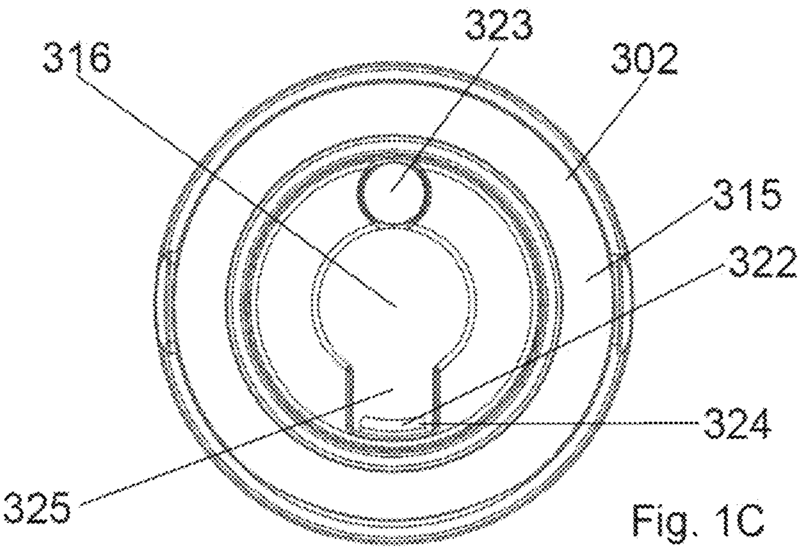
Figure 1D:
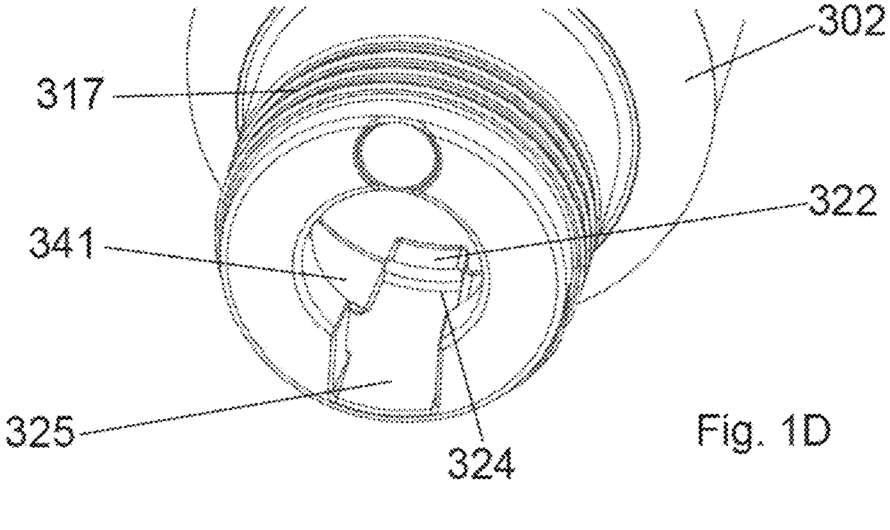
Figure 1E:
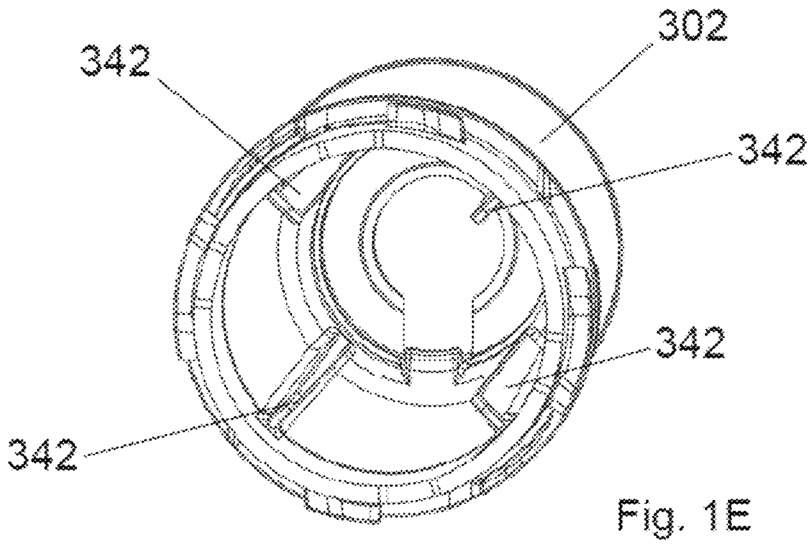

FIGS. 1C through 1F show additional views of the cartridge holder 302. FIG. 1C shows a view from the distal end. As is immediately apparent, the angular dimension of the fixing feature 322 is less than the one of the opening 325. The radial dimension of the fixing feature 322 or the fixing surface is less than the one of the opening 325 as well. From FIG. 1D, which shows the distal end as well but in a perspective view, it can be gathered that the cartridge holder, in particular the distal region 317, is reinforced, i.e. has a higher wall strength or thickness, in a region which is angularly adjacent to the fixing feature 322. A reinforcement section 341 extends circumferentially in the interior of the cartridge holder. The reinforcement section may axially overlap with the fixing feature. The reinforcement section 341 may be arranged distally offset from the fixing feature 322 alternatively or additionally. In the region of the interior of the cartridge holder which angularly overlaps with the fixing feature the reinforcement section is preferably interrupted to promote radial deformability of the cartridge holder when the head portion displaces the fixing feature 322 radially.

Figure 1F:
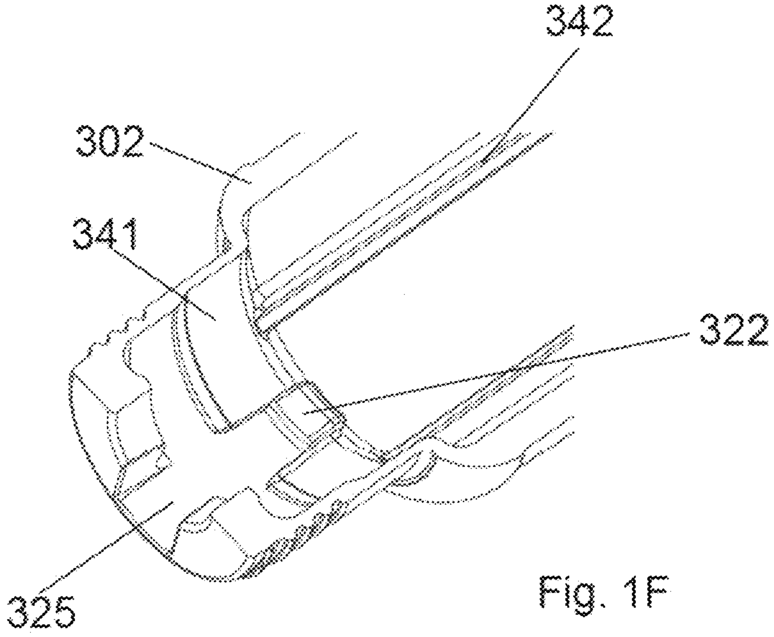

As seen from the opening 325 axially towards the fixing surface 324, the wall thickness of the cartridge holder 302 may be less than the wall thickness in the reinforcement section 341. The wall thickness of the cartridge holder 302 in the region of the fixing feature 322 and defined by the fixing feature may be greater than the one in the reinforcement section 341. The fixing feature 322 may radially protrude over the reinforcement section 341. The reinforcement section 341 is also depicted in FIG. 1F which shows a perspective sectional view of the cartridge holder 302. In this figure as well as in FIG. 1E, which shows a view from the proximal end of the cartridge holder 302, it is shown that the interior of the cartridge holder comprises a plurality of circumferentially disposed, preferably equally spaced, spacer features or cartridge support features 342, e.g. ribs. The features 342 are axially oriented. The features 342 may be provided to radially support the cartridge, e.g. the main body portion 311 thereof, if the cartridge is retained in the cartridge holder. These features may be the only difference between a cartridge holder which receives cartridges with a smaller diameter and one which receives a cartridge with greater diameter. The cartridge holder for the larger diameter cartridge may, expediently, not have the cartridge support features 342. Thus, the exterior dimensions of the cartridge holder may be the same although the exterior diameters of the cartridges retained in the cartridge holders are different.

As is apparent from the figures, e.g. from FIG. 1B, the needle connector 319, e.g. a thread, is distally offset from the fixing feature 322. Specifically, the region between the fixing feature and the cartridge guiding feature or sloped surface 326 may be free of the needle connector 319. The needle connector may axially overlap with the cartridge guiding feature 326 or be provided distally offset from this feature 326. Thus, the axial extension of the needle connector 319 may be less than in other cartridge holder designs. For example, the needle connector 319 may be restricted to a distal section of the distal region 317 of the cartridge holder, where between the needle connector 319 and the main body region a connector-free region is arranged. The axial extension of the connector-free region may be greater than 50% of the axial extension of the distal section with the needle connector. The axial extension of the distal section with the needle connector may be greater than the one of the connector-free region. As the cartridge holder in the region between the fixing feature 322 and the guiding feature 326 has a reduced wall thickness to increase the inner diameter of the cartridge holder 302, e.g. in order to maintain a given outer contour or dimension of the cartridge holder 302, providing an additional radial indentation on the exterior in this region, which would be required for the needle connector 319, would increase the risk of damaging the cartridge holder in this region or even render it un-moldable. Thus, the shortened needle connector is advantageous.

Although the depicted embodiment shows only one fixing feature, a sloped surface may also be provided in case a plurality of fixing features is used. In the following embodiment, the sloped surface is not shown, however.

FIGS. 2A to 2D show cross-sections of the cartridge 301 and the cartridge holder 302 and various load paths which can occur within the cartridge holder 302 when the cartridge 301 is moved in the distal or in the proximal direction.

As described above in the region where the fixing feature 322 is provided, e.g. the distal region 317, the cartridge holder 302 may be radially deformable. Thus, the inner diameter may be increased when the cartridge holder 302 is exposed to a radially outwardly directed force. An axial and/or radial force acts on the fixing feature 322, e.g. while the head portion is guided along and in contact with the fixing feature 322, the cartridge holder 302 is widened on account of the rigidity of the fixing feature 322. After the head portion 310 has passed the fixing feature 322, the fixing feature is displaced inwardly again, e.g. on account of the deformation being an elastic deformation, and the cartridge surface 313 and the fixing surface 324 are arranged as depicted in FIG. 1B.

A disassembly of the cartridge 301 due to tampering or impact is likely to involve the cartridge 301 moving in the proximal direction relative to the cartridge holder 302. In this situation, a surface of the septum retainer 309 facing in the proximal direction may contact the fixing feature 322 and apply a load to the cartridge 301 generally directed proximally. This load may cause deformation of the cartridge holder 302. The fixing feature 322 is likely to flex in the proximal direction.

Figure 2A:
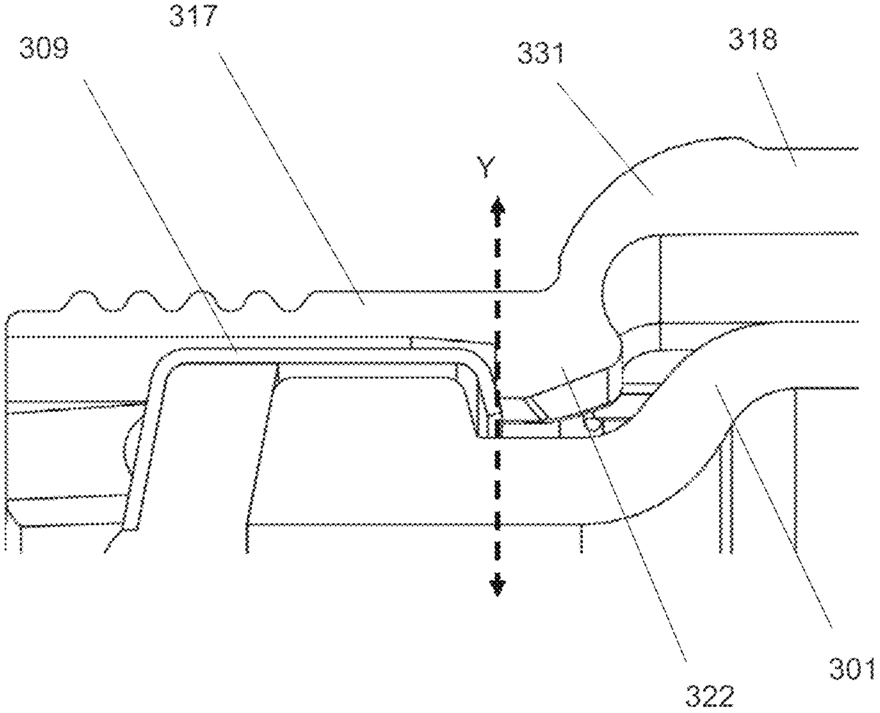
FIGS. 2A to 2D show schematic cross-sections of the cartridge assembly in order to illustrate the technical problem on which the disclosure is based on and the various load paths which can occur at the cartridge holder.

However, the fixing feature 322 may also flex either inwards or outwards radially, approximately in the direction of the Y-axis which is oriented perpendicular to the distal and proximal direction, see dashed arrow line in FIG. 2A. The flexing of the fixing feature 322 may not precisely follow the indicated direction of the Y-axis, but it is generally inwardly or outwardly with respect to the longitudinal axis of the device.

This deflection in the radial direction of the Y-axis has an influence on the fixing strength. In the situation of outwards radial flexion along the Y-axis as the load increases, the radial engagement of the fixing feature 322 with the septum retainer 309 will decrease. If the load is high enough, the engagement will decrease to a point at which the septum retainer 309 slips past the fixing feature 322 and/or the fixing feature 322 deforms plastically to allow disassembly of the cartridge 301. In addition, the septum retainer 309 is likely to have a fillet at its outer edge which will come into contact with the fixing feature 322 at some point as the engagement decreases, hastening the disassembly process. The result is likely to be a low fixing strength. In the situation of inwards radial flexion as the load increases the radial engagement of the fixing feature 322 with the septum retainer 309 will increase. The behavior is therefore 'self-locking' and this will tend to provide a higher fixing force. In addition, the fixing strength is likely to be less sensitive to the size of the initial engagement and therefore less likely to vary due to cartridge 301 or cartridge holder 302 tolerances.

Figure 2B:
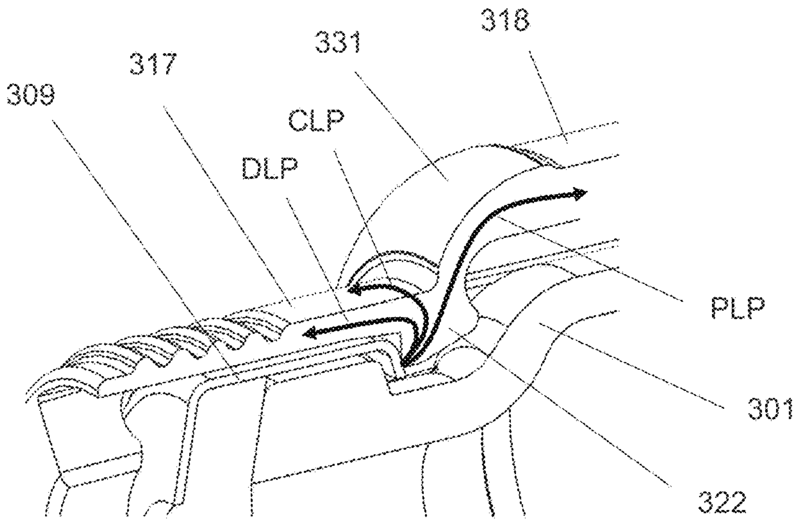

The radial deflection of the fixing feature 322 inwardly or outwardly in the direction of the Y-axis is dependent to the load path taken by the load applied to the fixing feature 322 by the cartridge septum retainer 309. As an example, three possible load paths, a distal load path DLP, a circumferential load path CLP and a proximal load path PLP within a cartridge holder 302 are indicated in FIG. 2B. The amount of load extending along each load path DLP, CLP, PLP will depend on the stiffness of the corresponding load path DLP, CLP, PLP, whereas a higher stiffness load path absorbs more load than a low stiffness load path.

If the cartridge 301 is inserted into the opening 325 of the cartridge holder 302 in the distal direction at some point the most distal surface of the cartridge 301 passes the fixing feature 322.

Via the opening 305, the cartridge 301 can be inserted into the cartridge holder. A dispensing end 306 of the cartridge may be inserted or introduced into the cartridge through the opening 305. The opposite end of the cartridge holder is the distal end of the cartridge holder 302, which may be that end which is arranged closest to the dispensing end 306 of the cartridge 301. The distal end of the cartridge holder is preferably designed to retain the cartridge in the holder, e.g. by abutment, such that the cartridge may only leave the cartridge holder through the opening 305.

If the cartridge 301 is inserted fully into the cartridge holder, such that the distal end of the cartridge holder 302 is closest to the dispensing end 306 of the cartridge, the distal end of the fixing feature 322 retains the cartridge 301 in the holder. During insertion the cartridge 301 passes the fixing feature 322 and applies a distal load to the fixing feature 322. This leads to a distal load path DLP, and a circumferential load path CLP, which acts also in the distal region 317. When the cartridge 301 is moved from the retained position in the proximal direction the cartridge 301 applies through the septum retainer 309 a load to the fixing feature which leads to the proximal load path PLP. The septum retainer 309 acts then in the proximal direction towards the fixing feature 322 which leads to a load and the proximal load path PLP as indicated in FIG. 2B.

Each load path DLP, CLP, PLP will tend to create a different deflection mode. Two key load paths DLP, PLP with very different deflection modes are shown in isolation at FIGS. 2C and 2D.

Figure 2C:
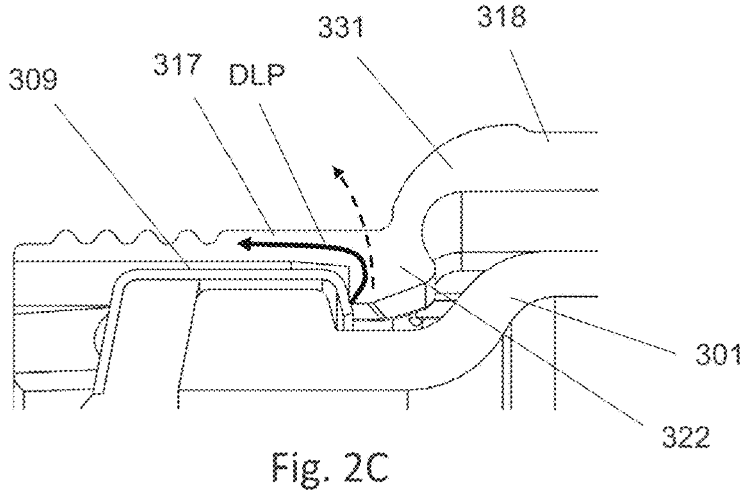

As shown in FIG. 2C the distal load path DLP tends to result in outwards radial flexion of the fixing feature 322, as indicated by the dashed arrow.

Figure 2D:
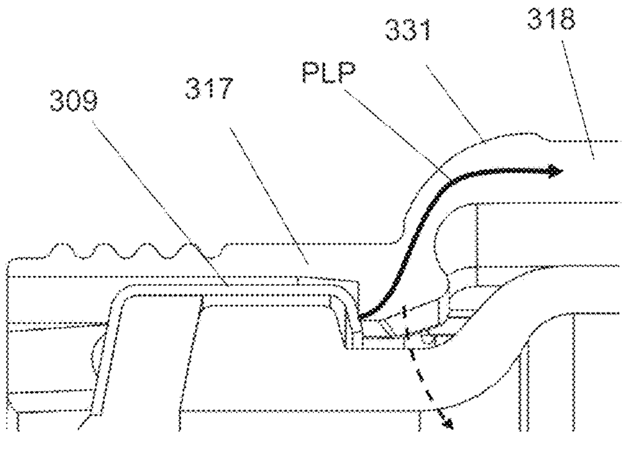

As shown in FIG. 2D a proximal load PLP path tends to result in inwards radial flexion of the fixing feature, as indicated by the dashed arrow The distal load paths DLP, CLP will tend to cause outwards radial deflection, whereas the proximal load path PLP will tend to cause inwards radial deflection.

Figure 3A:
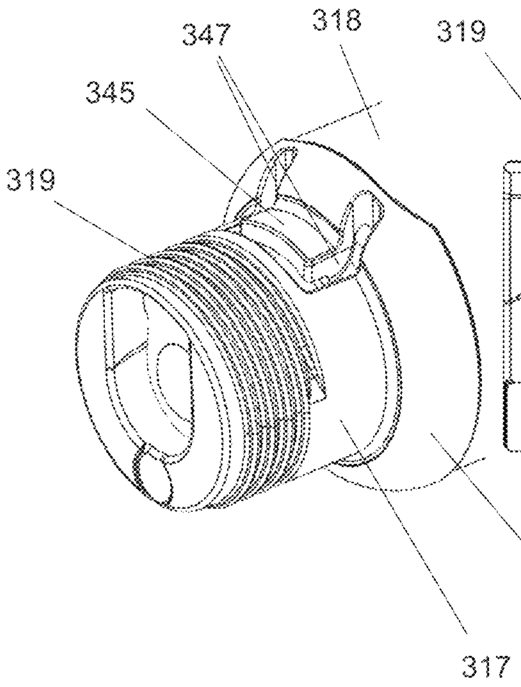
FIGS. 3A and 3B show a schematic 3D-view and a schematic cross-section of a section of the cartridge assembly with a flexible arm.
Figure 3B:
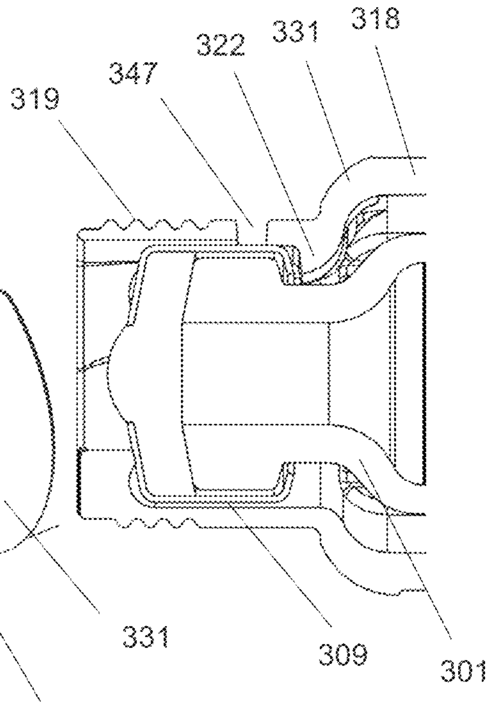

FIGS. 3A and 3B show a schematic 3D-view and a cross-section of the cartridge and the cartridge holder with a flexible arm as known from the prior art.

A flexible arm 345 which extends in the distal region 317 of the cartridge holder 302 may be used to create a self-locking behavior. The flexible arm 345 extends in the proximal direction into the shoulder region 331. The flexible arm 345 is fixed at the shoulder region 331 and is flexible in the direction radially inwardly and outwardly. The flexible arm 345 is framed by a u-shaped opening 347. However, this concept has some downsides. Firstly, its function as a cartridge fixing feature is obvious to an observer viewing the external surfaces of the part. Secondly, it is accessible for manipulation with a narrow bladed tool such as a screwdriver. Thirdly, it has a limited radial stiffness because of the inherent flexibility of the flexible arm 345. This makes it easier to manipulate the flexible arm 345 so that it no longer retains the cartridge 301 effectively.

Figure 4A:
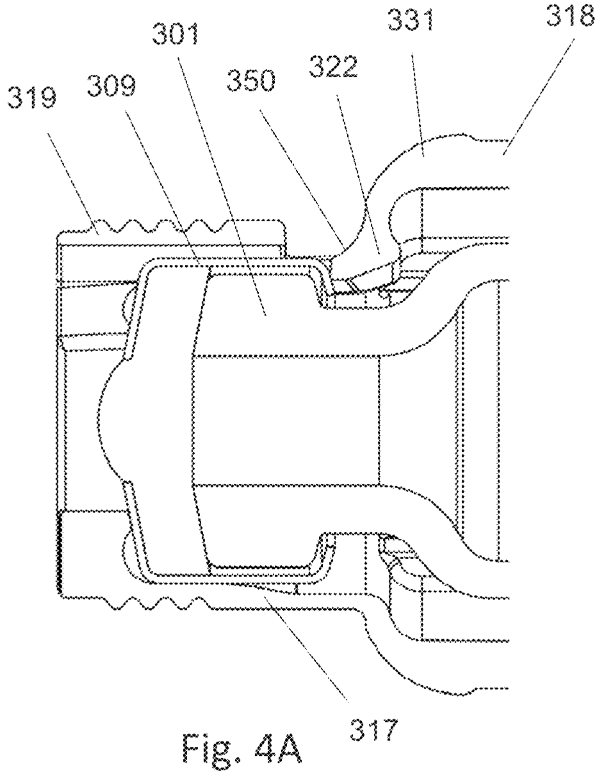
FIGS. 4A to 4C show schematic 3D-views and a schematic cross-section of a section of the distal part of the cartridge assembly of the first embodiment.
Figure 4B:
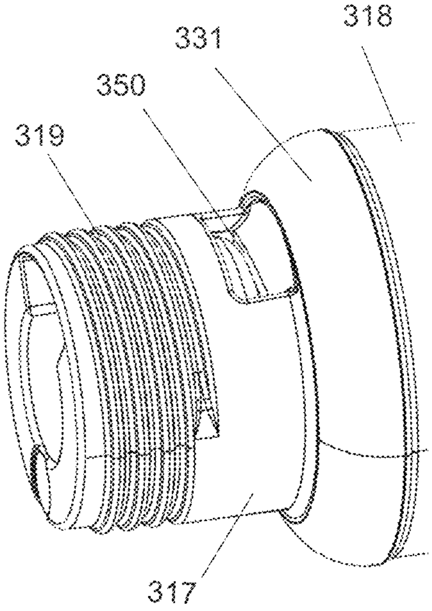
Figure 4C:
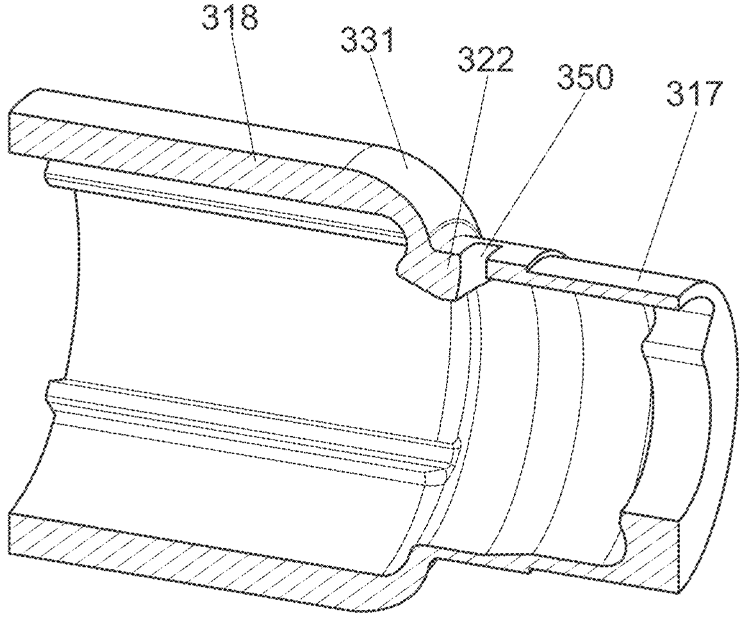

FIGS. 4A to 4C show schematic 3D-views and a cross-section of the distal part of the cartridge holder of the first embodiment.

FIG. 4A shows a schematic cross-sectional view of the distal region 317 and a part of the main body region 318 of the cartridge holder 302 as well as the cartridge 301 arranged in the cartridge holder 302. Between the distal region 317 of the cartridge holder 302 and the main body region 318 a shoulder region 331 is arranged.

Adjacent to this shoulder region 331 a region with reduced mechanical stiffness 350 which is positionally fixed, which comprises an aperture, is arranged. The purpose of the region with reduced mechanical stiffness 350 is to reduce or eliminate the load emerging from the cartridge 301 towards the fixing feature 322 via a distal load path DLP, CLP when the cartridge 301 is moving in the proximal direction and therefore its tendency to flex radially outwards. This therefore increases the amount of load travelling through the proximal load path PLP with its associated inwards radial deflection. The region with reduced mechanical stiffness 350 comprises in this embodiment an aperture. The addition of the aperture provides self-locking behavior and increases the fixing strength significantly.

In addition, by reducing or removing the distal load paths DLP, CLP, the stiffness of the cartridge holder 302 in response to proximal loading from the cartridge 301 is reduced. This means that during an impact loading scenario, the forces generated will also be reduced because the impact energy can be absorbed over a longer deflection distance. This also tends to increase fixing strength.

The aperture may extend radially through a sidewall of the cartridge holder, particularly through the entire sidewall from the exterior of the cartridge holder to the interior of the cartridge holder. The aperture may be arranged in and/or restricted to the distal region of the cartridge holder. The aperture may extend and/or be oriented circumferentially, for example as a slit. The aperture may be arranged parallel to the connection feature, which may be a thread. The aperture within the sidewall of the cartridge holder may be defined by a molding tool which during production may abut, in particular radially, an outer surface of a core pin of the molding tool, the core pin defining the interior of the cartridge holder in that region, in which the aperture is arranged, e.g. the distal region. In this way, without changing the core pins for the interior of the cartridge holder, the fixing feature may be defined.

Certain aspects are therefore an improvement over what is known in the field in terms of the tamper resistance to prevent unauthorized disassembly of the cartridge 301, because the fixing feature is less visually obvious and less accessible to manipulation by tools.

FIG. 4B shows a schematic 3D-view of the distal region 317 of the cartridge holder 302, the shoulder region 331 and a small section of the main body region 318. It also shows the region with reduced mechanical stiffness 350 adjacent to the shoulder region 331 in the distal direction.

FIG. 4C shows a schematic 3D-view of a longitudinal cross-section of the cartridge holder 302.

Figure 5A:
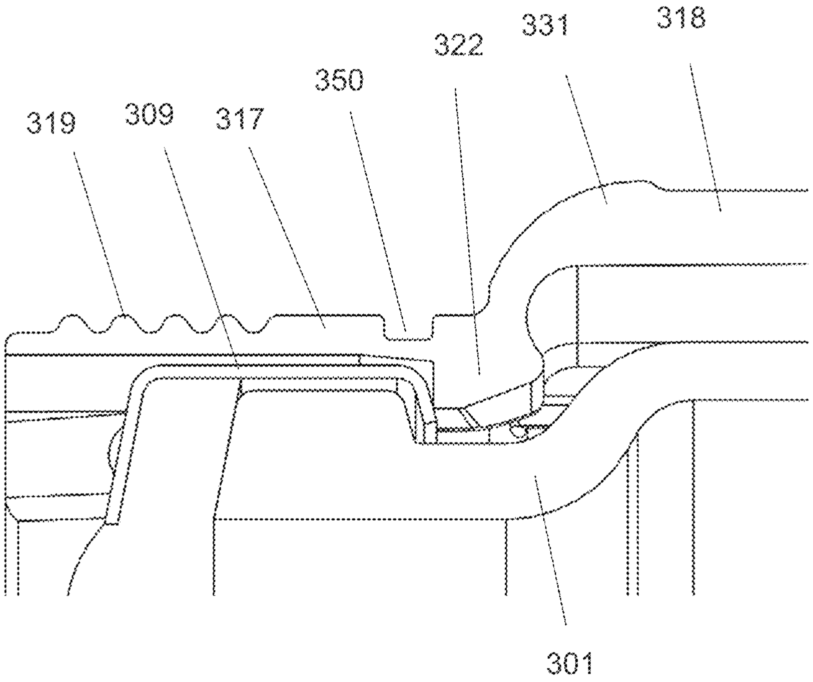
FIGS. 5A and 5B show a schematic cross-section and a schematic 3D-view of the distal part of the cartridge assembly of a second embodiment.
Figure 5B:
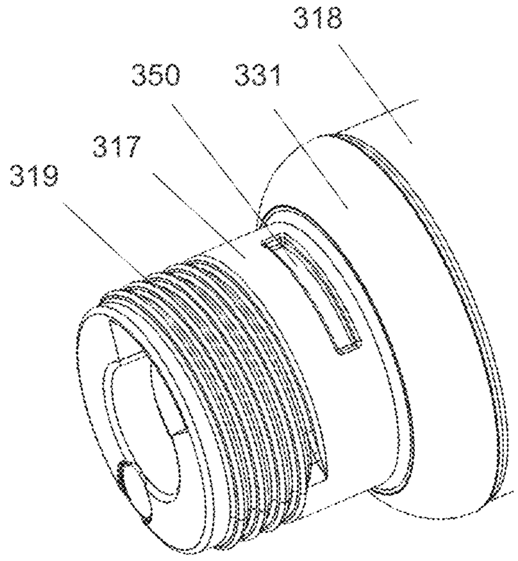

FIG. 5A shows a schematic cross-sectional view of a section of each the distal region 317, a part of the main body region 318 of the cartridge holder 302 as well as the cartridge 301 arranged in the cartridge holder 302.

The amount of load travelling along each load path DLP1, DLP2, PLP depends on the stiffness of the load path. A higher stiffness load path absorbs more load than a low stiffness load path. Adjusting the amount of stiffness can be achieved by varying the sized and the depth of the aperture which is positioned similar to the aperture of the previous embodiment. This region of reduced stiffness may take many forms and involve profiling of both the inner and outer surfaces, either as well as or instead of an aperture. A simple example using reduced wall thickness which may be in the form of a groove.

An additional advantage of this design is that the tamper resistance of the fixing method is further increased, as external manipulation of the fixing feature is made even more difficult by the lack of an aperture.

Figure SB shows a schematic 3D-view of the distal region 317, the shoulder region 331 and a section of the main body region 318 of the cartridge holder 302. At the distal region 317 a region with reduced stiffness 350 in the form of a rectangular groove is shown. The groove is arranged adjacent to the shoulder region 331. The longer side of the rectangle extends parallel to the shoulder region.

Figure 6A:
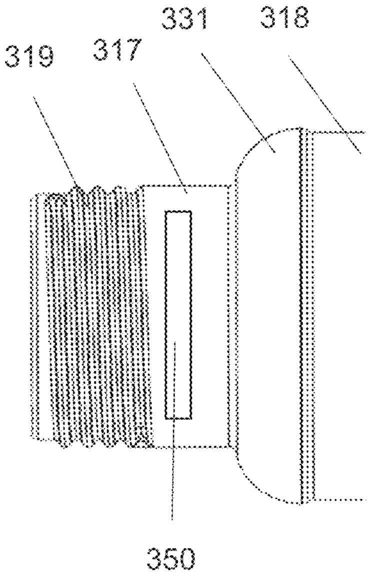
FIGS. 6A to 6C show a schematic views the distal part of the cartridge assembly of the first or second embodiment.
Figure 6B:
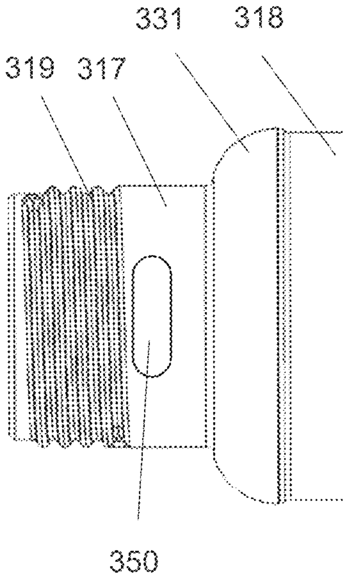
Figure 6C:
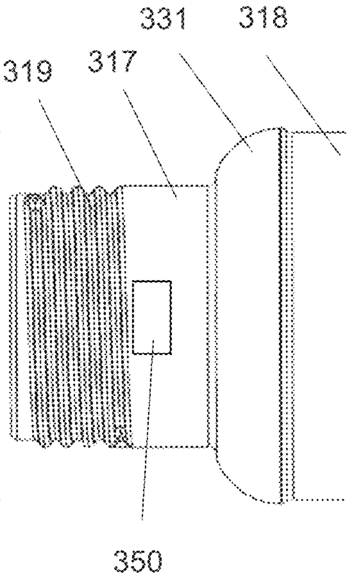

FIGS. 6A to 6C show a schematic cross-sectional views the distal region 317 of the cartridge holder 302 of the first or second embodiment. It shows several examples of possible shapes of the aperture which can be rectangular with or without rounded edges. These examples are not exclusive, there could be also other shapes such as circular or triangular shapes, that form a region with reduced stiffness leading to desired load path.

Figure 7A:
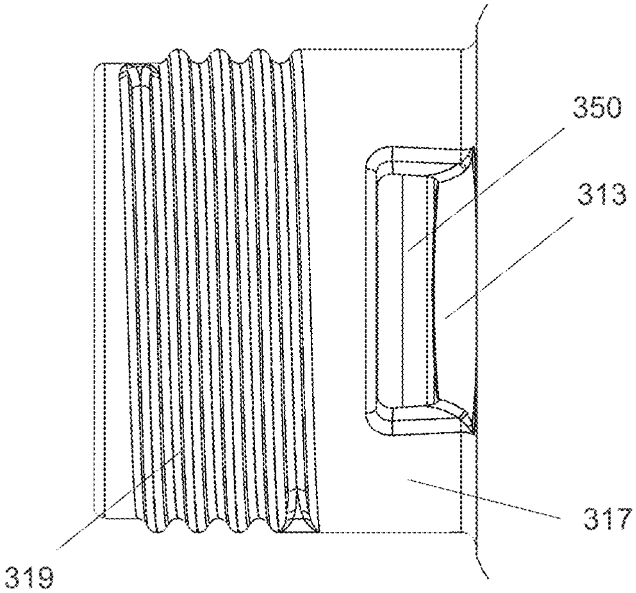
FIGS. 7A and 7B show schematic views of preferred embodiments of the contact face of the fixing feature.
Figure 7B:
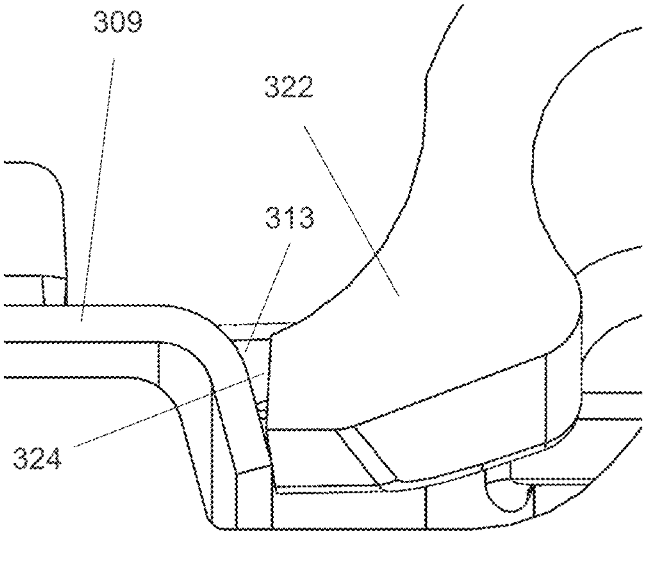

FIGS. 7A to 7B show schematic views of preferred embodiments of the contact face of the fixing feature.

The concept also includes several additional features which serve to increase the self-locking behavior.

The fixing surface 324 of the fixing feature 322 may be convex curve so that the contact with the cartridge septum retainer 309 will preferentially be made at the center of the fixing surface 324.

This is shown in a schematic cross-sectional view in FIG. 7A. This may provide an increase in the self-locking behavior.

Alternatively, as shown in a cross sectional view of the fixing feature 322 and a section of the septum retainer 309 in FIG. 7B, the fixing surface 324 may be angled such that contact with the cartridge septum retainer 309 will preferentially be made at the radially inboard edge of the fixing feature 322. This may provide an increase in the self-locking behavior. In addition, the septum retainer 309 geometry tends to be more uniform at smaller radii, providing improved consistency of behavior.

Figures 8A, 8B:
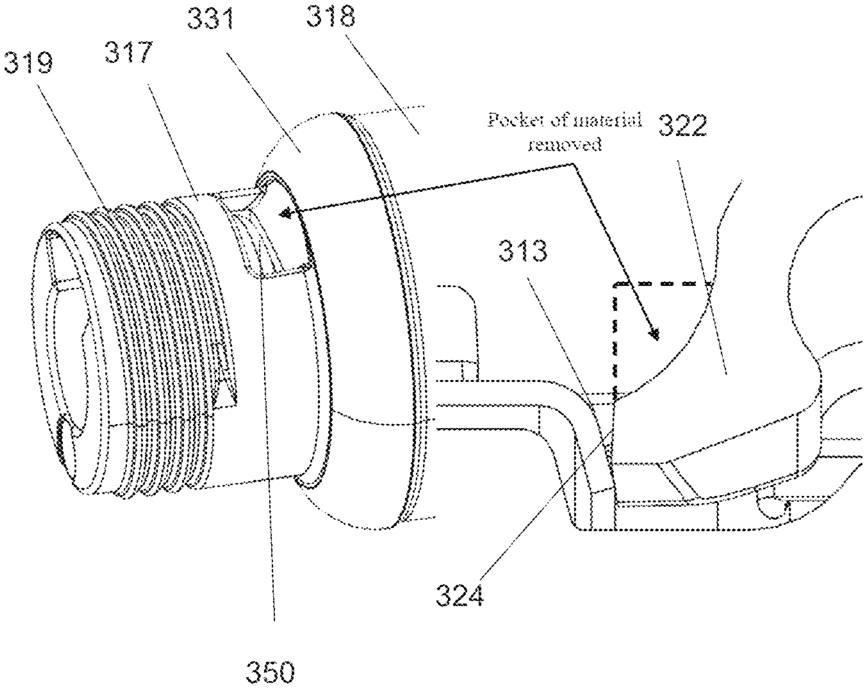
FIGS. 8A and 8B show schematic 3D-views the distal region and the fixing feature.

FIGS. 8A and 8B show schematic 3D-views of the distal region 317 and of the fixing feature 322 where a pocket of material has been removed in a region radially outboard of the fixing feature 322.

This may provide an increase in the self-locking behavior. An additional advantage of the aperture is that the force required to assemble the cartridge into the cartridge holder 302 is reduced, due to the increased flexibility of the fixing feature provided by the aperture.

Figure 9A:
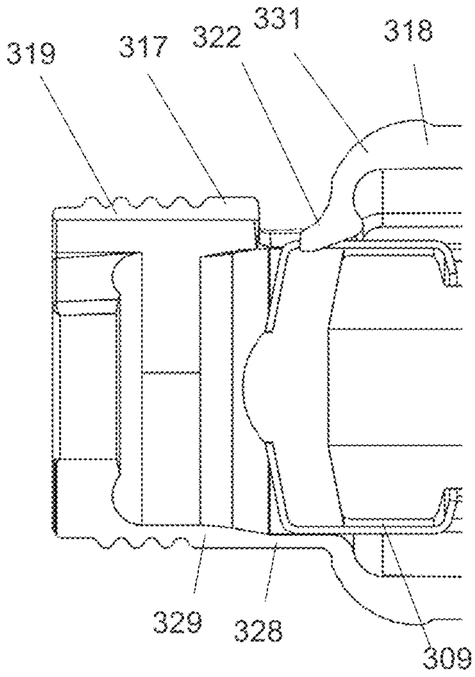
FIGS. 9A to 9C show schematic cross-sectional views of embodiments maintaining the seal integrity.
Figure 9B:
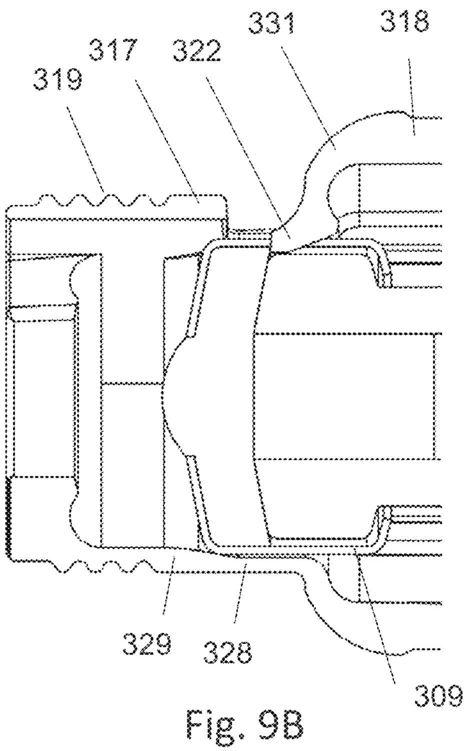
Figure 9C:
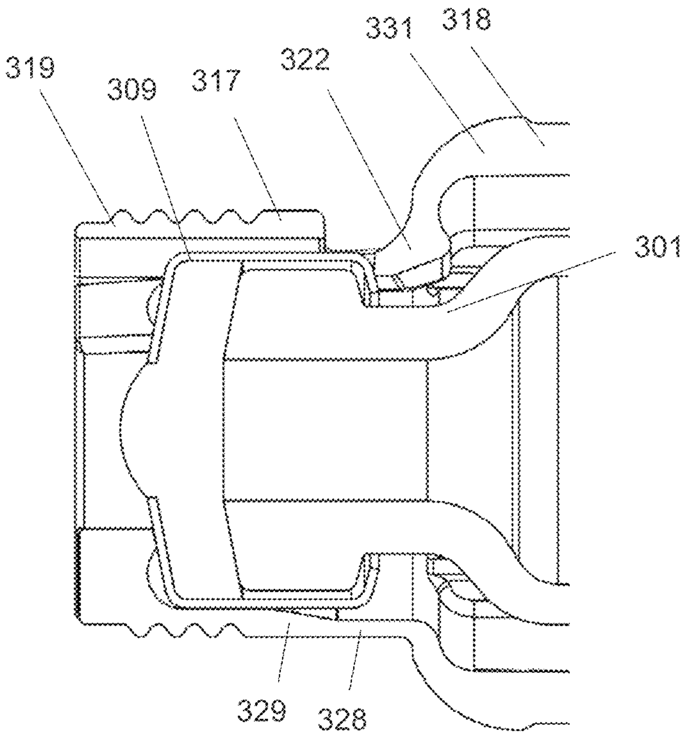

FIGS. 9A to 9C show schematic cross-sectional views of embodiments maintaining the seal integrity.

In 1.5 mL and 3 mL cartridges 301, the septum retainer 309 is supported over part of its length by the septum 308 and part of its length by the cartridge glass. High radial contact pressures applied to the region supported only by the septum 308 are more likely to compromise seal integrity than contact pressures applied to the region supported by the cartridge glass, as the septum 308 is softer and is also the component that provides the sealing interface.

To address this risk, the internal bore of the cartridge holder needle hub includes a first 328 and a second 329 internal diameter with a conical surface connecting them together. The first internal diameter 328 may be larger than the second internal diameter 329, whereas the second internal diameter 329 may be arranged distal in view of the first internal diameter 328.

This geometry is intended to reduce the interference between the septum retainer 309 and the fixing feature 322 whilst the fixing feature 322 is contacting the region of the septum retainer 309 that is supported by the septum 308, reducing the likelihood of seal integrity being compromised.

As the septum retainer 309 gains support from the glass, the septum retainer 309 transitions to contacting on the conical face, increasing interference now that the septum retainer 309 is better able to resist deformation. Towards the end of the assembly stroke and in the final assembled state, the septum retainer 309 contacts on the region with smaller diameter 329, thus providing increased interference and therefore fixing strength. This design therefore allows for greater assembly interference, which is likely to improve fixing strength, whilst minimizing the risk of seal integrity being compromised.

FIG. 9A shows an assembly process stage 1. While inserting the cartridge 301 into the cartridge holder 302 through the opening 305 in the distal direction at some point the distal part of the cartridge 301 contacts the fixing feature 322. The fixing feature 322 deflects outwardly, on the opposite side of the fixing feature 322 inside the cartridge holder 302 the cartridge 301 glides along the internal sidewall of the cartridge holder 302 and a contact occurs with a larger diameter 328 surface whilst the fixing feature is contacting the septum retainer surface that is supported by the septum, giving reduced interference and therefore contact pressure on the weaker part of the septum retainer. So, on the opposite side of the fixing feature 322 inside the cartridge holder 302 the cartridge 301 glides along the internal sidewall of the cartridge holder 302.

FIG. 9B shows an assembly process stage 2. If the cartridge is moved further in the distal direction the internal diameter of the cartridge holder 302 decreases, so that the cartridge 301 is forced in a press-fit like contact with the inner wall of the cartridge holder 302. Contact transitions to progressively smaller diameter surface as fixing feature contacts the septum retainer surface that is supported by the cartridge glass, giving increased interference.

FIG. 9C shows an assembly process stage 3. If the cartridge is moved even further in the distal direction the septum retainer 309 passes the fixing feature 322 completely. The fixing feature 322 then deflects radially inwardly to that it abuts the cartridge 301 from moving in the proximal direction. The distal part of the septum retainer 309 is encompassed from the cartridge holder 302 at the region with an internal smaller diameter 329.

Figure 10:
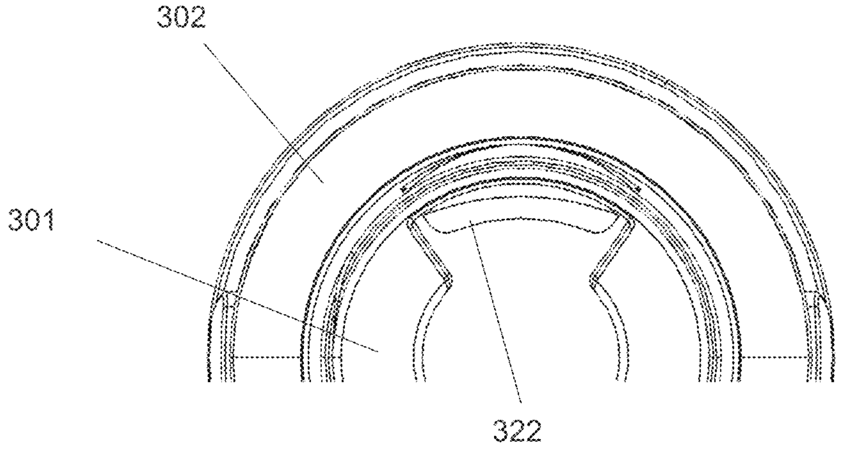
FIG. 10 shows a schematic view of an embodiment of a preferred shape of the fixing feature.

FIG. 10 shows a schematic view of an embodiment of a preferred shape of the fixing feature 322.

Figure 11A:
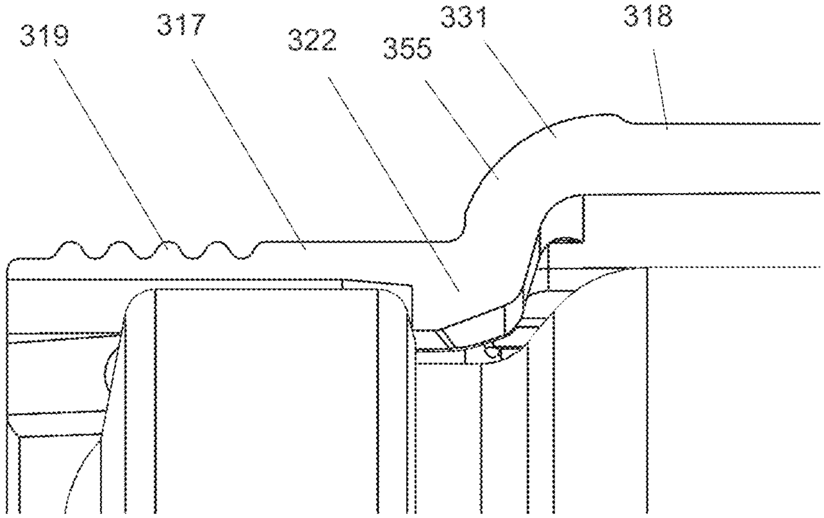
FIGS. 11A and 11B show a schematic views the distal part of the cartridge and the cartridge holder with a part with increased stiffness.
Figure 11B:
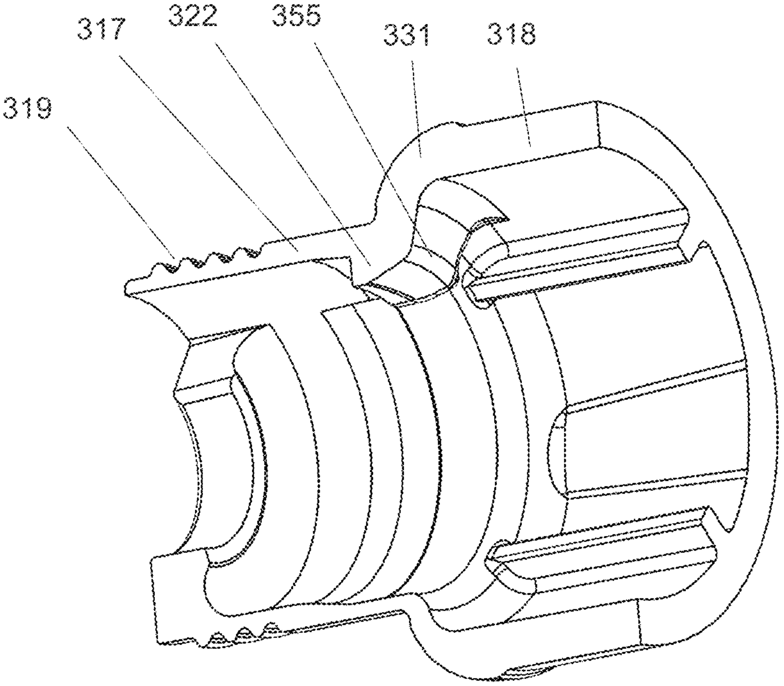

As an additional feature to reduce the peak localized contact pressure on the septum retainer and the risk to seal integrity, the fixing feature is also profiled so that interference peaks at the center of the feature, and reduces towards the edges FIGS. 11A to 11B show a schematic cross-sectional view and a schematic 3D-view of a cut of the distal part of the cartridge holder. Alternatively, the aim that the tamper resistance of the retention method is further increased, as external manipulation of the retention feature is made even more difficult by the lack of an opening. This may be achieved by incorporating a region of increased stiffness 355 into the proximal load path (rather than reduced stiffness into the distal load path). For example the fixing feature 322 may be thickened or comprise an additional layer for increasing the stiffness locally.

Figure 12:
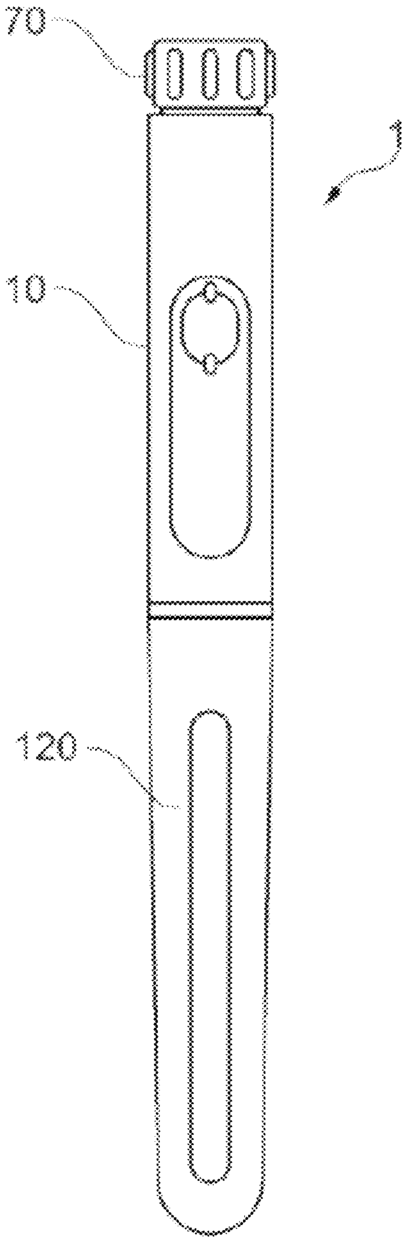
FIG. 12 illustrates an embodiment of a drug delivery device with a cap covering the distal end of the device prior to a dose setting operation.
Figure 13:
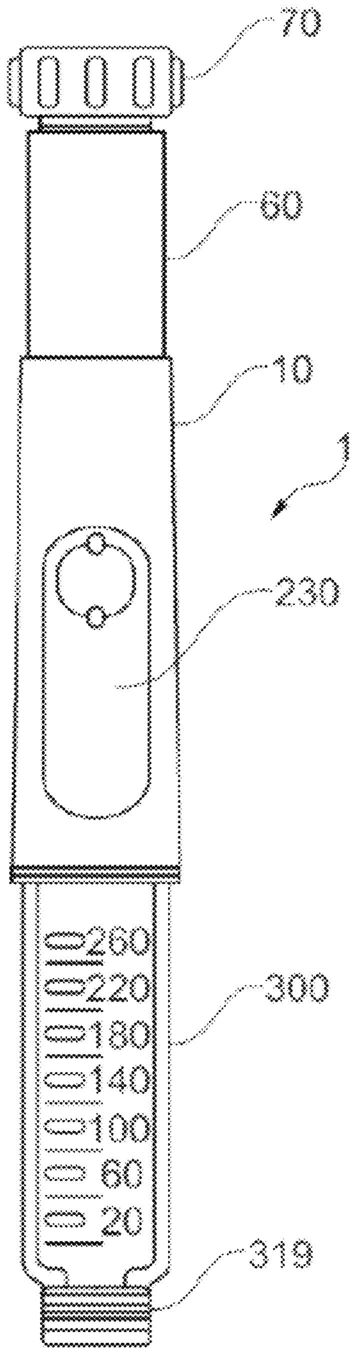
FIG. 13 illustrates the device of FIG. 5 where the cap has been removed to uncover the distal end of the cartridge assembly.

FIGS. 12 and 13 schematically illustrate embodiments of a drug delivery device suitable to be used in conjunction with the disclosed cartridge assembly. FIG. 12 shows the device 1 in a condition where a cap 120 is attached and covers the cartridge assembly 300. In FIG. 13 the cap has been removed. The cartridge assembly 300 is, expediently releasably, connected to a main body or housing 10 of the drug delivery device 1 as depicted in FIG. 13. The housing expediently defines the outer contour of the device and may be formed sleeve-like. A needle unit can be connected to the needle connector 319 in order to dispense drug or medicament from the device 1. A dose setting member 70 is movably retained in the housing 10 and can be manipulated by the user to set a dose. For example, it can be rotated relative to the housing to set a dose. The device may be a variable dose device, where the size of the dose is not predetermine by the design of the drive mechanism retained in the housing but rather may be changed by the user. In FIG. 13, a dose set condition of the drug delivery device is illustrated, where the numeral (not depicted) shown in window 230 is changed as compared to FIG. 12 such that it illustrates the size of the currently set dose. The device may be designed such that, during dose setting, the dose setting member 70 is displaced proximally relative to the housing 10. Alternatively, the dose setting member may stay in the same axial position independently of the set dose. From the position depicted in FIG. 13, a dispensing action may be initiated, expediently by moving or exerting a force in the distal direction onto the dose setting member 70 or a dose dispensing member provided in a proximal end section of the drug delivery device 1. To dispense the dose, the bung is displaced distally relative to the cartridge, e.g. by a piston rod of the device (not explicitly shown). In the interior of the housing a cartridge bias member may be arranged (not explicitly shown) such as a spring washer or a resilient cushion, e.g. of rubber. The bias member may bias the cartridge distally into contact with a proximal surface of the cartridge holder, e.g. the inner surface of the distal end wall 315. The bias member may abut the cartridge, e.g. the cartridge body, directly, e.g. the proximal end thereof to transfer its load onto the cartridge, or indirectly via a rigid spacer component.

The current design is intended for use in retaining 1.5 mL and 3 mL cartridges within their Cartridge Holders. However, it may easily be adapted to retain any cartridge, ampule or container within a housing where the benefits of simple assembly, high fixing strength and improved tamper resistance are required.

The scope of protection is not limited to the examples given herein above. Any invention disclosed herein is embodied in each novel characteristic and each combination of characteristics, which particularly includes every combination of any features which are stated in the claims, even if this feature or this combination of features is not explicitly stated in the claims or in the examples.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes): carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

REFERENCE NUMERALS

300 cartridge assembly
301 cartridge
302 cartridge holder
303 cartridge retaining section
304 inner wall
305 opening
306 dispensing end
307 drug/medicament
308 septum
309 septum retainer
310 head portion
311 main body portion
312 neck portion
313 cartridge surface
314 shoulder surface
315 distal end wall
316 opening
317 distal region
318 main body region
319 needle connector
320 connection region
321 step
322 fixing feature
323 injection gate
324 fixing surface
325 opening
326 surface
327 opening
328 region with first internal diameter
329 region second internal diameter
331 shoulder region
340 cartridge body
341 reinforcement section
342 cartridge support feature
1 drug delivery device
120 cap
70 dose setting member
10 housing
230 window
A thickness
B distance
PLP proximal load path
DLP distal load path
CLP circumferential load path
Y axis perpendicular to distal or proximal direction
345 flexible arm
347 U-shaped cavity
350 Region with reduced mechanical stiffness
355 Region with increased mechanical stiffness

The invention claimed is:

1. A cartridge assembly for a drug delivery device, the cartridge assembly comprising:

a cartridge containing a drug, a cartridge holder, the cartridge holder defining an interior cartridge holding section, wherein the cartridge is arranged within the cartridge holding section, wherein the cartridge holder comprises a distal region with a needle connector arranged at a distal end of the distal region and a main body region, a fixing feature arranged at the distal region, and a region with a reduced mechanical stiffness compared to a stiffness of the main body region, wherein the region with the reduced mechanical stiffness is integrated into the distal region and arranged between the needle connector and the fixing feature, such that, when the cartridge is moved in a proximal direction, an emerging load is transferred from the cartridge to the fixing feature and further to the main body region in the proximal direction, wherein the fixing feature comprises a continuous mechanical connection to the distal region of the cartridge holder in a circumferential direction, and wherein the fixing feature is arranged such that movement of the cartridge in a proximal direction causes a radial inward deflection of the fixing feature.

2. The cartridge assembly of claim 1, wherein the region with the reduced mechanical stiffness comprises a groove or an aperture.

3. The cartridge assembly of claim 2, wherein the groove or the aperture comprises a rectangular or rounded rectangular shape.

4. The cartridge assembly of claim 1, wherein the fixing feature comprises a fixing surface which is arranged to abut a cartridge surface of the cartridge to prevent removal of the cartridge from the cartridge holder such that the cartridge is permanently secured in the cartridge holder.

5. The cartridge assembly of claim 4, wherein the cartridge surface is a proximal surface which faces away from a dispensing end of the cartridge, wherein the cartridge surface is arranged between the dispensing end of the cartridge and an end opposite of the dispensing end, and wherein the fixing feature is integrated into the cartridge holder.

6. The cartridge assembly of claim 5, wherein the cartridge comprises a head portion with the dispensing end and a main body portion, wherein a neck portion of a reduced diameter is provided between the head portion and the main body portion, the cartridge surface being a surface delimiting the head portion axially.

7. The cartridge assembly of claim 4, wherein the fixing feature protrudes from an interior wall of the cartridge holder in a radial direction, and wherein the cartridge holder is configured such that the fixing feature can be resiliently displaced in the radial direction.

8. The cartridge assembly of claim 4, wherein the fixing surface comprises an elevation which faces towards the cartridge surface.

9. The cartridge assembly of claim 4, wherein the fixing surface is oriented relative to the cartridge surface, such that the fixing surface and the cartridge surface are facing each other and are not parallel.

10. The cartridge assembly of claim 1, wherein the fixing feature comprises a region with a reduced thickness.

11. The cartridge assembly of claim 1, wherein the cartridge holding section comprises at least three interior regions, i.e. a first region, a fixing feature region, and a second region, wherein the fixing feature is arranged in the fixing feature region and wherein the fixing feature region is arranged between the first region and the second region in an axial direction, wherein an inner diameter or clear span of the cartridge holder in the fixing feature region is less than an inner diameter or clear span in the first region and in the second region, and wherein the first region and the second region have different inner diameters or clear spans.

12. The cartridge assembly of claim 11, wherein one of the first region and the second region comprises a distal interior region which is arranged distally to the fixing feature, wherein the distal interior region comprises two regions with two different inner diameters, and wherein the region with the smaller diameter of the two different inner diameters is arranged distally to the region with the larger inner diameter of the two different inner diameters.

13. The cartridge assembly of claim 1, wherein the cartridge holder is closed in a radial direction along the entire angular or azimuthal extension of the fixing feature and along the entire axial extension of the fixing feature.

14. The cartridge assembly of claim 1, wherein the cartridge holder comprises cumulatively to the region with reduced mechanical stiffness another region with an increased mechanical stiffness which is arranged adjacent to a fixing surface in the proximal direction and decreases a radial flexibility of the cartridge holder in the other region such that a movement of the cartridge in the proximal direction is impeded.

15. The cartridge assembly of claim 1, wherein the fixing feature is formed unitarily with a section of the cartridge holder, wherein the section defines or forms an exterior surface or outer contour of the cartridge holder in at least one region of the cartridge holder.

16. The cartridge assembly of claim 1, wherein the region with reduced mechanical stiffness is restricted to a region distally away from the fixing feature.

17. A drug delivery device comprising:

a housing; and a cartridge assembly releasably connected to the housing; wherein the cartridge assembly comprises:

a cartridge containing a drug, a cartridge holder, the cartridge holder defining an interior cartridge holding section, wherein the cartridge is arranged within the cartridge holding section, wherein the cartridge holder comprises a distal region with a needle connector arranged at a distal end of the distal region and a main body region, a fixing feature arranged at the distal region, and a region with a reduced mechanical stiffness compared to a stiffness of the main body region, wherein the region with the reduced mechanical stiffness is integrated into the distal region and arranged between the needle connector and the fixing feature, such that, when the cartridge is moved in a proximal direction, an emerging load is transferred from the cartridge to the fixing feature and further to the main body region in the proximal direction;

wherein the drug comprised in the cartridge is a medicament, wherein the fixing feature comprises a continuous mechanical connection to the distal region of the cartridge holder in a circumferential direction, and wherein the fixing feature is arranged such that movement of the cartridge in a proximal direction causes a radial inward deflection of the fixing feature.

18. The drug delivery device of claim 17, wherein the region with the reduced mechanical stiffness comprises a groove or an aperture.

* * * * *